US007553661B2

(12) United States Patent
Galipeau et al.

(10) Patent No.: US 7,553,661 B2
(45) Date of Patent: Jun. 30, 2009

(54) STROMAL ANTIGEN-PRESENTING CELLS AND USE THEREOF

(75) Inventors: Jacques Galipeau, Town of Mount-Royal (CA); John Stagg, Montréal (CA)

(73) Assignee: McGill University, Montréal, Québec (CA)

( * ) Notice: Subject to any disclaimer, the term of this patent is extended or adjusted under 35 U.S.C. 154(b) by 0 days.

(21) Appl. No.: 11/415,166

(22) Filed: May 2, 2006

(65) Prior Publication Data

US 2006/0269526 A1 Nov. 30, 2006

Related U.S. Application Data

(60) Provisional application No. 60/685,493, filed on May 31, 2005.

(51) Int. Cl.
C12N 5/06 (2006.01)
C12N 5/08 (2006.01)
(52) U.S. Cl. ...................... 435/325; 424/93.7
(58) Field of Classification Search ............... None
See application file for complete search history.

(56) References Cited

U.S. PATENT DOCUMENTS 7,195,758 B2 * 3/2007 Schultze et al. .......... 424/93.71

OTHER PUBLICATIONS

Singh et al., Nature Biotechnology, 1999, 17: 1075-1081.*
Pittenger et al. Science. "Multilineage Potential of Adult Human Mesenchymal Stem Cells", Apr. 2, 1999, pp. 143-147.
Deans et al. "Mesenchymal stem cells: Biology and potential clinical uses", Exp Hematol. Aug. 28, 2000, pp. 875-884.
Yoon et al. "Clonally expanded novel multipotent stem cells from human bone marrow regenerate myocardium after myocardial infarction", Clin Invest. Feb. 2005;115 (2)pp. 326-338.
Pittenger et al. "Mesenchymal stem cells and their potential ac cardiac therapeutics", Circ Res. Jul. 9, 2004;95(1) pp. 9-20.
Horwitz et al. "Isolated allogeneic bone marrow-derived mesenchymal cells engraft and stimulate growth in children with osteogenesis imperfecta . . . " Proc Natl Acad Sci U S A. Jun. 25, 2002;99(13) pp. 8932-8937.
Wang et al. "Adult stem cells from bone marrow stroma differentiate into airway epithelial cells: Potential therapy for cystic fibrosis", Proc Natl Acad Sci U S A. Jan. 4, 2005;102(1)pp. 186-191.
Batholomew et al. "Baboon mesenchymal stem cells can be genetically modified to secrete human erythropoietin In Vivo", Hum Gene Ther. Aug. 10, 2001;(12)pp. 1527-1541.
Chuah et al. "Long-term persistence of human bone marrow stromal cells transduced with Factor VIII-retroviral vectors and transient production of therapeutic levels . . . ", Hum Gene Ther. Mar. 20, 2000;11(5)pp. 729-738.
Studeny et al. "Bone marrow-derived mesenchymal stem cells as vehicles for interferon-β delivery into tumors", Cancer Res. Jul. 1, 2002;62(13)pp. 3603-360.

Eliopoulos et al. "Human-compatible collagen matrix for prolonged and reversible systemic delivery of erythropoietin . . . " Mol Ther. Oct. 2004;10(4)pp. 741-748.
Stagg et al. "Marrow stromal cells for interleukin-2 delivery in cancer immunotherapy", Hum Gene Ther. Jun. 2004;15(6)pp. 597-608.
Koc et al. "Allogeneic mesenchymal stem infusion for treatment of metachromatic leukodystrophy (MLD) and Hurler syndrome (MPS-IH)", Bone Marrow Transplant. Aug. 2002;30(4)pp. 215-222.
Wakitani et al. "Myogenic cells derived from rat bone marrow mesenchymal stem cells exposed to 5-Azacytidine", Muscle Nerve. Dec. 1995;18(12)pp. 1417-1426.
Woodbury et al. "Adult rat and human bone marrow stromal cells differentiate into neurons", J Neurosci Res. Aug. 15, 2000;61(4)pp. 364-370.
Reyes et al. "Purification and ex vivo expansion of postnatal human marrow mesodermal progenitor cells", Blood. Nov. 1, 2001;98(9)pp. 2615-2625.
Leblanc et al. "HLA expression and immunologic properties of differentiated and undifferentiated mesenchymal stem cells", Exp Hematol. Oct. 2003;31(10)pp. 890-896.
Tse et al. "Suppression of allogeneic t-cell proliferation by human marrow stromal cells: implications in transplantation", Transplantation. Feb. 15, 2003;75(3)pp. 389-397.
Dinicola et al. "Human bone marrow stromal cells supress T-lymphocyte proliferation induced by cellular or nonspecific mitogenic stimuli", Blood. May 15, 2002;99(10)pp. 3838-3843.
Potian et al. "Veto-like activity of mesenchymal stem cells: Functional discrimination between cellular responses to alloantigens and recall antigens", J Immunol. Oct. 1, 2003;171 (7)pp. 3426-3434.
Gotherstrom et al. "Immunologic properties of human fetal mesenchymal stem cells", Am J Obstet Gynecol. Jan. 2004;190 (1)pp. 239-245.
Krampera et al. "Bone marrow mesenchymal stem cells inhibit the response of naive and memory antigen-specific T cells to their cognate peptide", Blood. May 1, 2003;101(9)pp. 3722-3729.
Djouad et al. "Immunosuppressive effect of mesenchymal stem cells favors tumor growth in allogeneic animals", Blood. Nov. 15, 2003;102(10)pp. 3837-3844.
Aggarwal et al. "Human mesenchymal stem cells modulate allogeneic immune cell responses", Blood. Feb. 15, 2005;105(4)pp. 1815-1822.
Glennie et al. "Bone marrow mesenchymal stem cells induce division arrest anergy of activated T cells", Blood. Apr. 1, 2005;105(7)pp. 2821-2827.
Beyth et al. "Human mesenchymal stem cells alter antigen-presenting cell maturation and induce T-cell unresponsiveness" Blood. Mar. 1, 2005;105(5)pp. 2214-2219.
Jiang et al. "Human mesenchymal stem cells inhibit differentiation and function of monocyte-derived dendritic cells", Blood. May 15, 2005;105(10)pp. 4120-4126.
Maccario et al. "Interaction of human mesenchymal stem cells with cells involved in alloantigen-specific immune response favors the differentiation of CD4 T-cell subsets expressing a regulatory/suppressive phenotype", Haematologica. Apr. 2005;90(4)pp. 516-525.

(Continued)

*Primary Examiner*—Ilia Ouspenski
(74) *Attorney, Agent, or Firm*—Bereskin & Parr LLP; Micheline Gravelle; Carmela DeLuca

(57) ABSTRACT

There is provided a stromal antigen-presenting cell capable of antigen presentation in the context of MHC II. When stimulated with IFNγ the stromal cell expresses B7-H1 and/or CD80. These stromal cells can be used to generate an immune response in an animal.

9 Claims, 22 Drawing Sheets

OTHER PUBLICATIONS

Lancet "Treatment of severe acute graft-versus-host disease with third party haploidentical mesenchymal stem cells", May 1, 2004;363 (9419)pp. 1439-1441.

Meisel et al. "Human bone marrow stromal cells inhibit allogeneic T-cell responses by indoleamine 2,3-dioxygenase-mediated tryptophan degradation", Blood. Jun. 15, 2004;103(12)pp. 4619-4621.

Le Blanc et al. "Mesenchymal stem cells inhibit the expression of CD25 (Interleukin-2 receptor) and CD38 on phytohaemagglutinin-activated lymphocytes", Scand J Immunol. Sep. 2004;60(3)pp. 307-315.

Shen et al. "Cloned dendritic cells can present exogenous antigens on both MHC class I and class II molecules", J Immunol. Mar. 15, 1997;158(6)pp. 2723-2730.

Reis E Sousa et al. "Major histocompatibility complex class I presentation of peptides derived from soluble exogenous antigen by a subset of cells engaged in phagocytosis", J Exp Med. Sep. 1, 1995;182(3)pp. 841-851.

Ohkuma et al. "Fluorescence probe measurement of the intralysosmal pH in living cells and the perturbation of pH by various agents", Proc Natl Acad Sci U S A. Jul. 1978;75(7):pp. 3327-3331.

Porgador et al. "Localization, quantitation, and in situ detection of specific peptide-MHC class I complexes using a monoclonal antibody", Immunity. Jun. 1997;6(6)pp. 715-726.

Canaday et al. "T-cell hybridomas from HLA-transgenic mice as tools for analysis of human antigen processing", J Immunol Methods. Oct. 1, 2003;281(1-2)pp. 129-142.

Nauta, Alma and Fibbe, Willem E.; "Immunomodulatory properties of mesenchymal stromal cells", Blood, 2007 110:3499-3508 (prepublished online Jul. 30, 2007).

Gieseke, Friederike, et al.; "Human multipotent mesenchymal stromal cells inhibit proliferation of PBMCs independently of IFN{gamma}R1 signaling and IDO expression". Blood, 2007 110:2197-2200 (prepublished online May 23, 2007).

LeBlanc, K. et al.; "Mesenchymal stem cells inhibit and stimulate mixed lymphocyte cultures and mitogenic responses independently of the major histocompatibility complex". 2003. Scandanavian Journal of Immunology, vol. 57, pp. 11-20.

Stagg, John, et al.; "Interferon-{gamma}-stimulated marrow stromal cells: a new type of nonhematopoietic antigen-presenting cell". Blood, 2006 107:2570-2577 (prepublished online Nov. 17, 2005).

Chan, Jennifer, et al.; "Antigen-presenting property of mesenchymal stem cells occurs during a narrow window at low levels of interferon-{gamma}". Blood. 2006 107:4817-4824 (prepublished online Feb. 21, 2006).

* cited by examiner

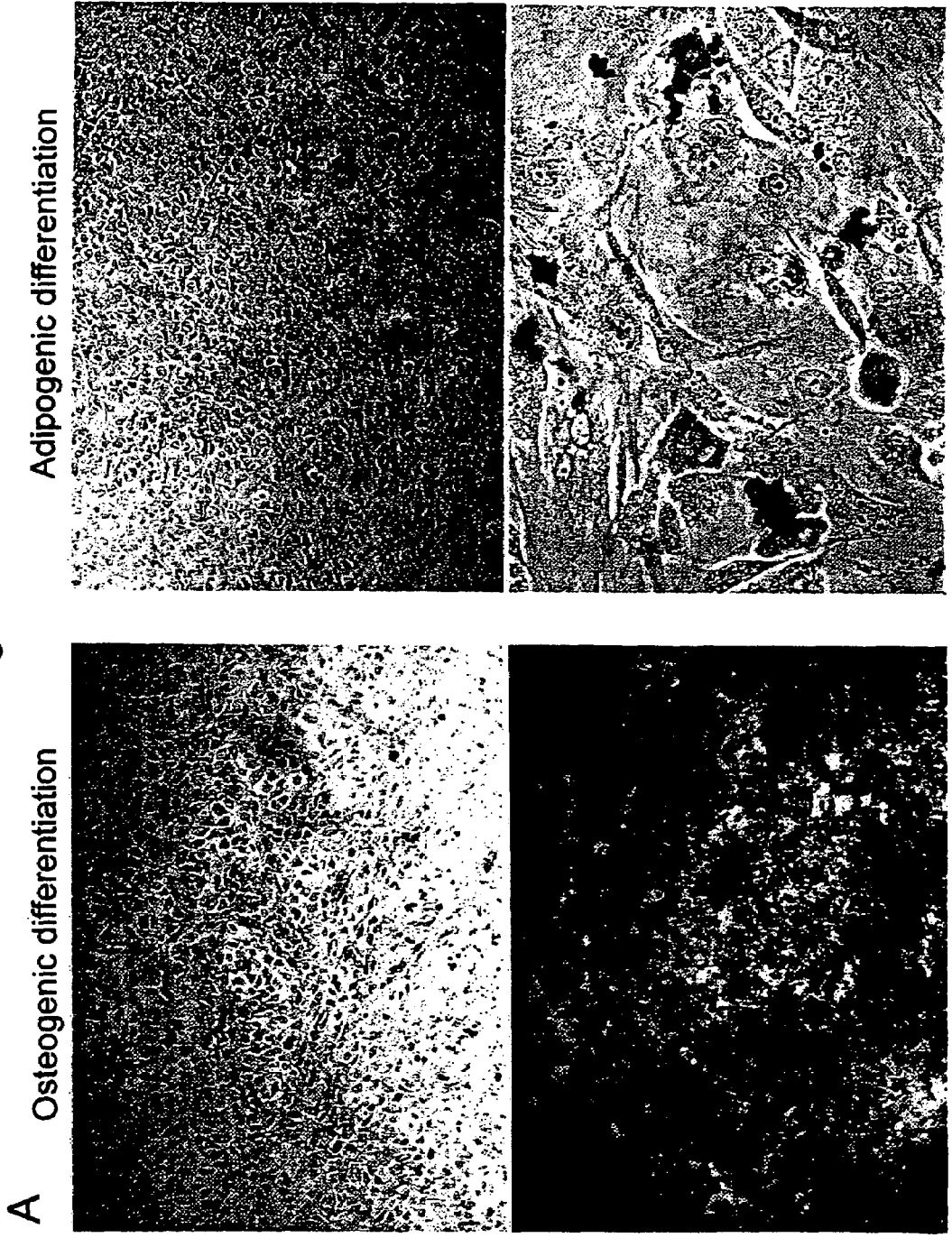

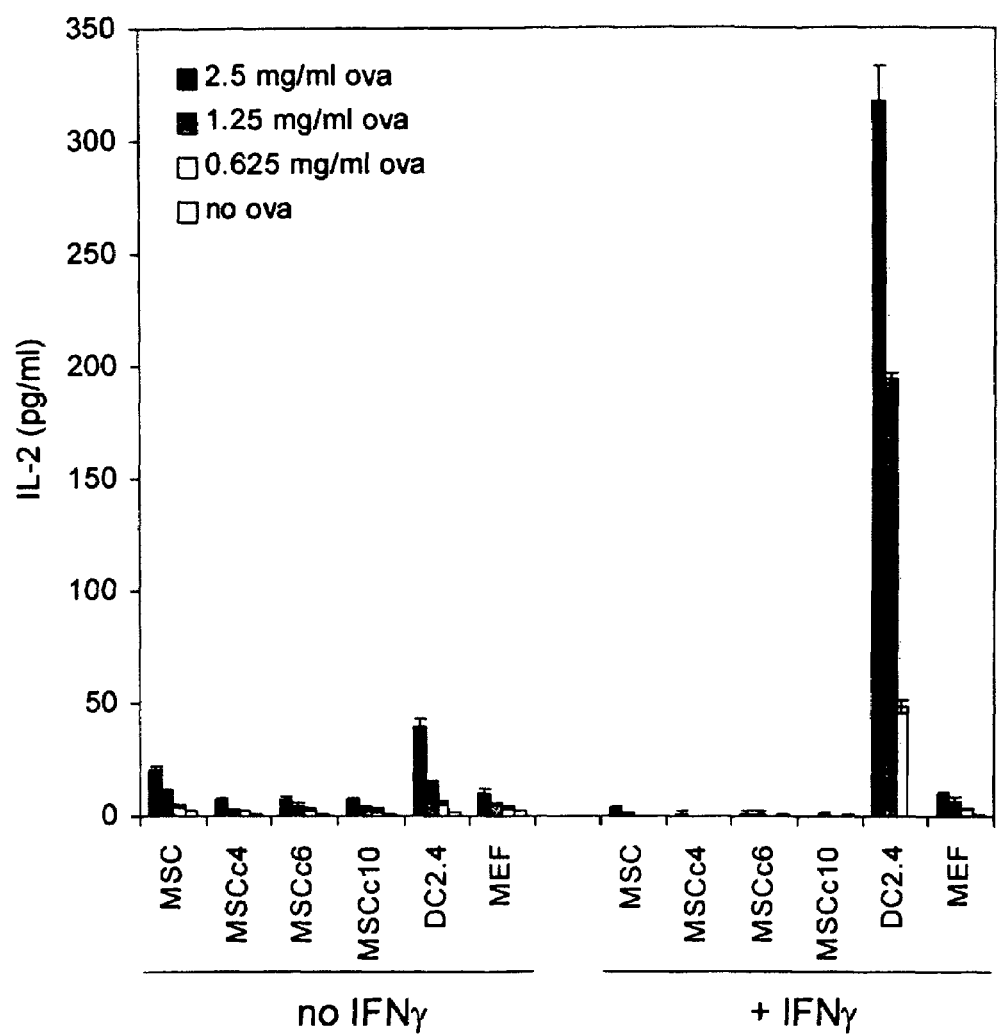

FIGURE 7A
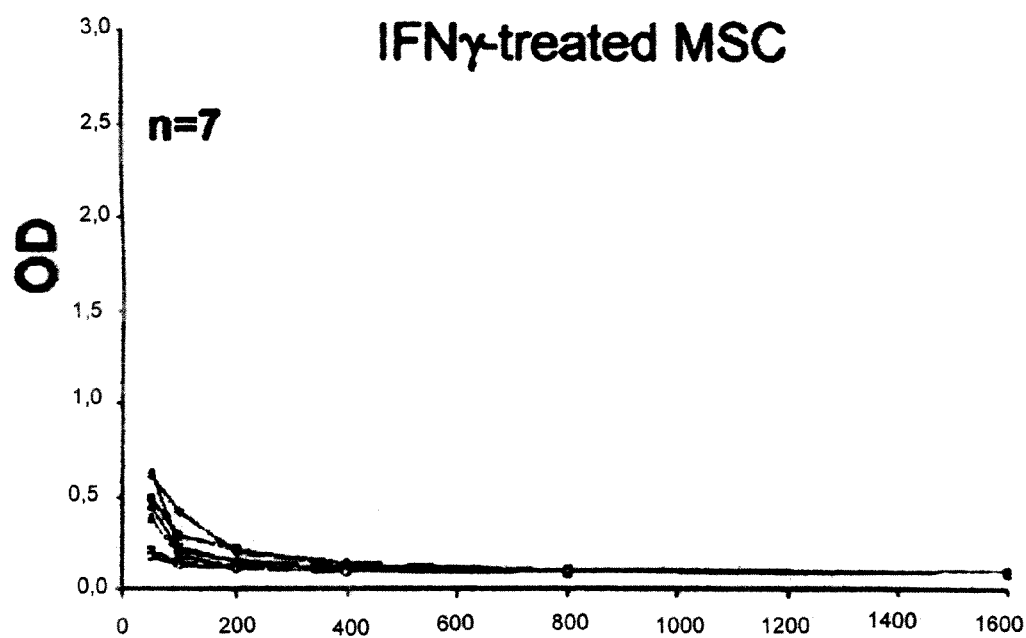
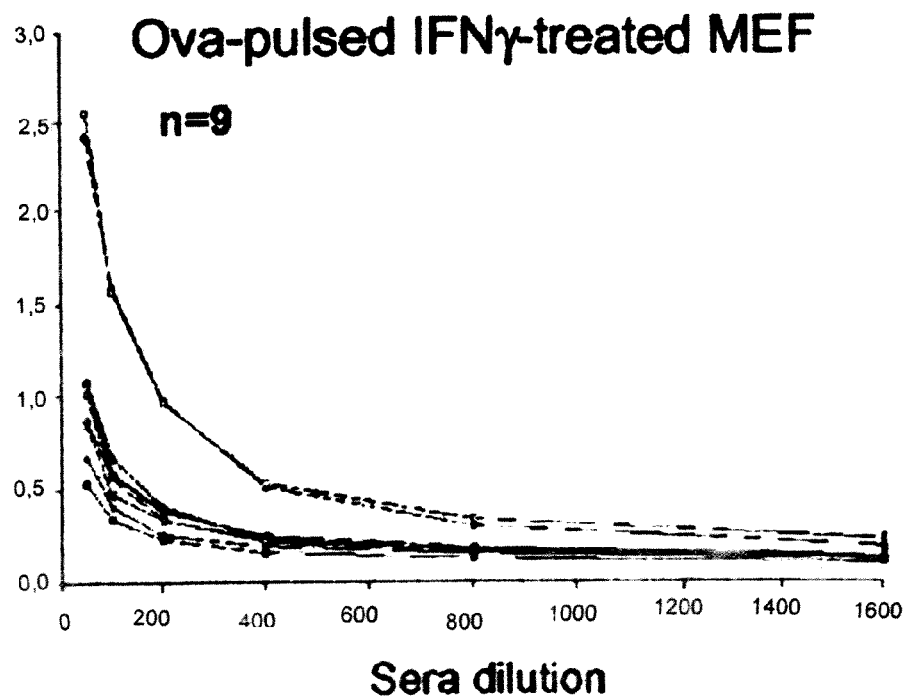

FIGURE 7B
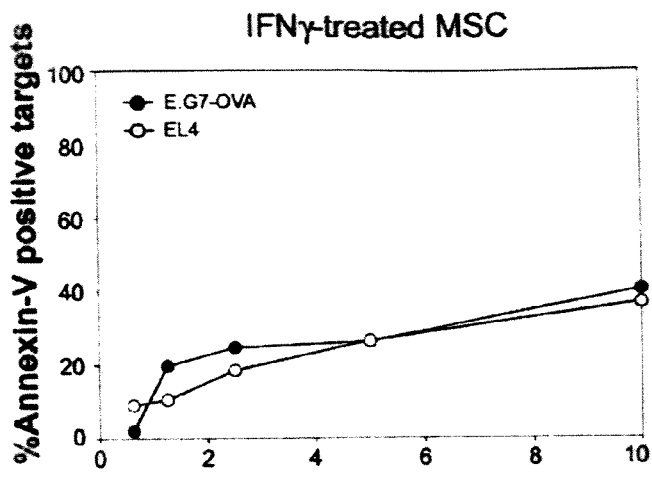
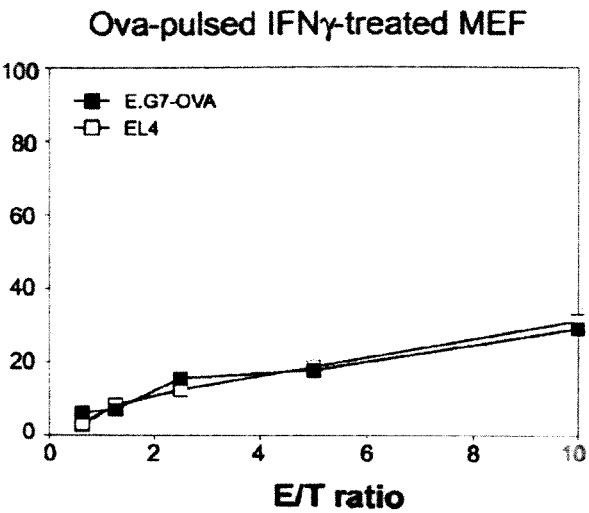
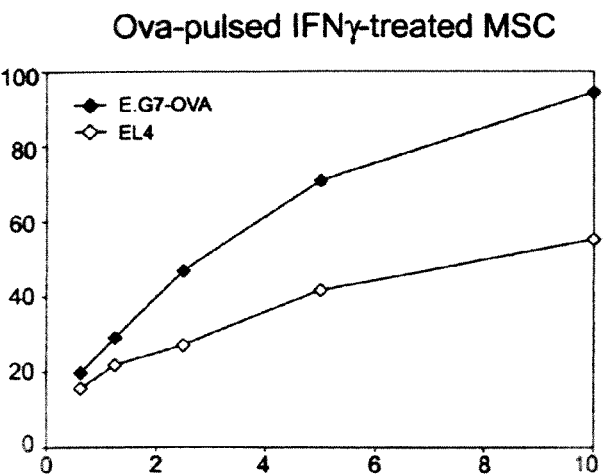

STROMAL ANTIGEN-PRESENTING CELLS AND USE THEREOF

CROSS REFERENCE TO RELATED APPLICATION

This application claims priority from U.S. provisional application No. 60/685,493 entitled STROMAL ANTIGEN-PRESENTING CELLS AND USE THEREOF, filed May 31, 2005.

FIELD OF THE INVENTION

This invention relates to antigen-presenting cells and their use in modulating immune response.

BACKGROUND OF THE INVENTION

Primary cultures of bone marrow stromal cells (MSCs) contain pluripotent cells with a robust ex vivo expansion capacity (Pittenger et al. Science. 1999 Apr. 2; 284 (5411): 143-7; Deans et al. Exp Hematol. 2000 August; 28(8):875-84). Pre-clinical and clinical studies have demonstrated that MSCs can be used for tissue repair (Yoon et al. Clin Invest. 2005 February; 115 (2):326-38; Pittenger et al. Circ Res. 2004 Jul. 9; 95(1):9-20), for in trans delivery of therapeutic gene products (Horwitz et al. Proc Natl Acad Sci USA. 2002 Jun. 25; 99(13):8932-7; Wang et al. Proc Natl Acad Sci USA. 2005 Jan. 4; 102(1):186-91; Batholomew et al. Hum Gene Ther. 2001 Aug. 10; 12(12):1527-41; Chuah et al. Hum Gene Ther. 2000 Mar. 20; 11 (5):729-38; Studeny et al. Cancer Res. 2002 Jul. 1; 62(13):3603-8; Eliopoulos et al. Mol Ther. 2004 October; 10(4):741-8; Stagg et al. Hum Gene Ther. 2004 June; 15(6):597-608) and for enhancing allogeneic hematopoietic stem cell engraftment (Koc et al. Bone Marrow Transplant. 2002 August; 30(4):215-22). Under specific culture conditions, MSCs can differentiate along multiple cell lineages, including adipocytes, chondrocytes, osteocytes, myocytes, astrocytes, neurons, endothelial cells and lung epithelial cells (Pittenger et al. Science. 1999 Apr. 2; 284 (5411): 143-7; Wakitani et al. Muscle Nerve. 1995 December; 18(12):1417-26; Woodbury et al. J Neurosci Res. 2000 Aug. 15; 61(4):364-70; Reyes et al. Blood. 2001 Nov. 1; 98(9): 2615-25; Wang et al. Proc Natl Acad Sci USA. 2005 Jan. 4; 102(1):186-91). Since no single surface marker has been described for purification, MSCs are generally isolated based on their adherence to tissue culture plates, resulting in a semi-homogenous population characterized by the absence of hematopoietic and endothelial surface markers such as CD45 and CD31, and by the expression of CD105, CD73 and CD44 (Pittenger et al. Circ Res. 2004 Jul. 9; 95(1):9-20). MSCs express low levels of major histocompatibility complex (MHC) class I molecules while, as a general rule, they do not constitutively express MHC class II molecules (LeBlanc et al. Exp Hematol. 2003 October; 31(10):890-6; Tse et al. Transplantation. 2003 Feb. 15; 75(3):389-97; DiNicola et al. Blood. 2002 May 15; 99(10):3838-43). One study, however, reported constitutive MHC class II expression on MSCs (Potian et al. J Immunol. 2003 Oct. 1; 171 (7):3426-34). Both MHC class I and class II molecules get upregulated following IFN$\gamma$ treatment, with a more heterogeneous expression between individual cells for MHC class II molecules (Gotherstrom et al. Am J Obstet Gynecol. 2004 January; 190 (1): 23945; LeBlanc et al. Exp Hematol. 2003 October; 31(10): 890-6; Krampera et al. Blood. 2003 May 1; 101(9):3722-9). Costimulatory molecules such as CD80, CD86, CD40 and CD40L are not known to be expressed nor induced on human MSCs, while mouse MSCs can be found to express CD80 (Krampera et al. Blood. 2003 May 1; 101 (9):3722-9).

MSCs are known to secrete a wide spectrum of growth factors and cytokines implicated in different aspects of hematopoiesis (Deans et al. Exp Hematol. 2000 August; 28(8):875-84). MSCs therefore possess properties of their own that may influence, positively or negatively, the desired therapeutic effect. One important feature of MSCs is their recently identified immunosuppressive properties against allogeneic immune responses. It has been shown that MSCs are able: (1) to suppress the proliferation of allogeneic T cells in response to mitogen or allogeneic cells (DiNicola et al. Blood. 2002 May 15; 99(10):3838-43; Djouad et al. Blood. 2003 Nov. 15; 102(10):3837-44; Krampera et al. Blood. 2003 May 1; 101(9):3722-9; Tse et al. Transplantation. 2003 Feb. 15; 75(3):389-97; LeBlanc et al. Exp Hematol. 2003 October; 31(10):890-6); (2) to inhibit the production of IFN$\gamma$ and tumor-necrosis factor (TNF)-$\alpha$ and increase the production of IL-10 (Aggarwal et al. Blood. 2005 Feb. 15; 105(4):1815-22); (3) to induce T cell division arrest anergy (Glennie et al. Blood. 2005 Apr. 1; 105(7):2821-7); (4) to inhibit the maturation and function of antigen presenting cells such as monocytes and dendritic cells (Beyth et al. Blood. 2005 Mar. 1; 105(5):2214-9; Jiang et al. Blood. 2005 May 15; 105(10): 4120-6); (5) to decrease alloantigen-specific cytotoxicity of CD8 T cells and natural killer (NK) cells; and (6) to favor the differentiation of CD4 T cells with presumed regulatory activity (Maccario et al. Haematologica. 2005 April; 90(4): 516-25). The clinical potential of the immunosuppressive properties of MSCs has been exemplified by LeBlanc and colleagues (Lancet. 2004 May 1; 363 (9419):1439-41) who reported in a case study that administration of haploidentical human MSCs following allogeneic stem cell transplantation could reverse the severe grade IV acute graft-versus-host disease (GVHD) of a patient. At present, the exact mechanism responsible for MSCs-mediated immunosuppression remains imprecise. Soluble factors such as hepatocyte growth factor (HGF), transforming growth factor (TGF)-$\beta$1 (DiNicola et al. Blood. 2002 May 15; 99(10):3838-43), indoleamine 2,3-dioxygenase (IDO) (Meisel et al. Blood. 2004 Jun. 15; 103(12):4619-21), IL-10 (Beyth et al. Blood. 2005 Mar. 1; 105(5):2214-9) and unidentified factors (Tse et al. Transplantation. 2003 Feb. 15; 75(3):389-97, Djouad et al. Blood. 2003 Nov. 15; 102(10):3837-44; Le Blanc et al. Scand J Immunol. 2004 September; 60(3):307-15), as well as contact-dependent mechanisms (Beyth et al. Blood. 2005 Mar. 1; 105(5): 2214-9; Krampera et al. Blood. 2003 May 1; 101(9):3722-9) have been implicated.

If the immunosuppressive effects of MSCs on allogeneic immune responses have been well described, the effect of MSCs on syngeneic immune responses has been largely overlooked.

A better understanding of the syngeneic immune response is desirable to exploit the immunogenic properties of MSCs.

SUMMARY OF THE INVENTION

Further features and advantages of the present invention will become apparent from the following detailed description, taken in combination with the appended drawings, in which:

In one embodiment of the invention there is provided an isolated stromal antigen-presenting cell. There is also provided a stromal antigen-presenting cell expressing a Major Histocompatibility Complex class II (MHCII) determinant.

In a further embodiment the stromal antigen-presenting cell of the invention expresses B7-H1 and/or CD80 molecules.

There is also provided an stromal antigen presenting cell which is capable of inducing secretion of IL-2 by T cells.

The stromal antigen-presenting cell of the invention can be obtained from bone marrow stromal antigen-presenting cell.

In another aspect of the invention the stromal antigen-presenting cell of the invention can be used to generate an immune response in an animal in need thereof.

There is also provided a method for producing stromal antigen-presenting cells comprising obtaining stromal cells from an animal; and stimulating the cells with IFNγ. In one embodiment the cell may be contacted with an antigen which can be selected for example from a peptide, carbohydrate, lipid, glycolipid, glycoprotein and nucleotide.

In yet another aspect of the invention there is provided a method for generating an immune response in an animal, comprising: providing stromal cells; stimulating the stromal cells with interferonγ (IFNγ); contacting the stimulated cells with an antigen; and introducing the stimulated cells into the animal.

The stromal antigen presenting cells of the invention can also be used for activating T cells by contacting the T cells with an IFNγ-stimulated stromal antigen-presenting cell that has been incubated with an antigen.

There is also provided a vaccine composition comprising the stromal antigen-presenting cell of the invention.

BRIEF DESCRIPTION OF THE DRAWINGS

Further features and advantages of the present invention will become apparent from the following detailed description, taken in combination with the appended drawings, in which:

FIG. 6 describes soluble ovalbumin antigen cross-presentation. C57BL/6 MSCs, DC2.4 or MEF ($5\times10^4$ cells) were cocultured for 20 hrs with ovalbumin-specific MHC class I-restricted T-T hybridomas (RF33.70; $10^5$ cells) in the presence of increasing doses of soluble ovalbumin. Where indicated, recombinant IFNγ (50 ng/ml final) was added to the cocultures. After 20 hrs, supernatant was collected and tested for IL-2 release by ELISA (Means of triplicates±standard deviations are shown);

DETAILED DESCRIPTION OF THE INVENTION

Figure 1:
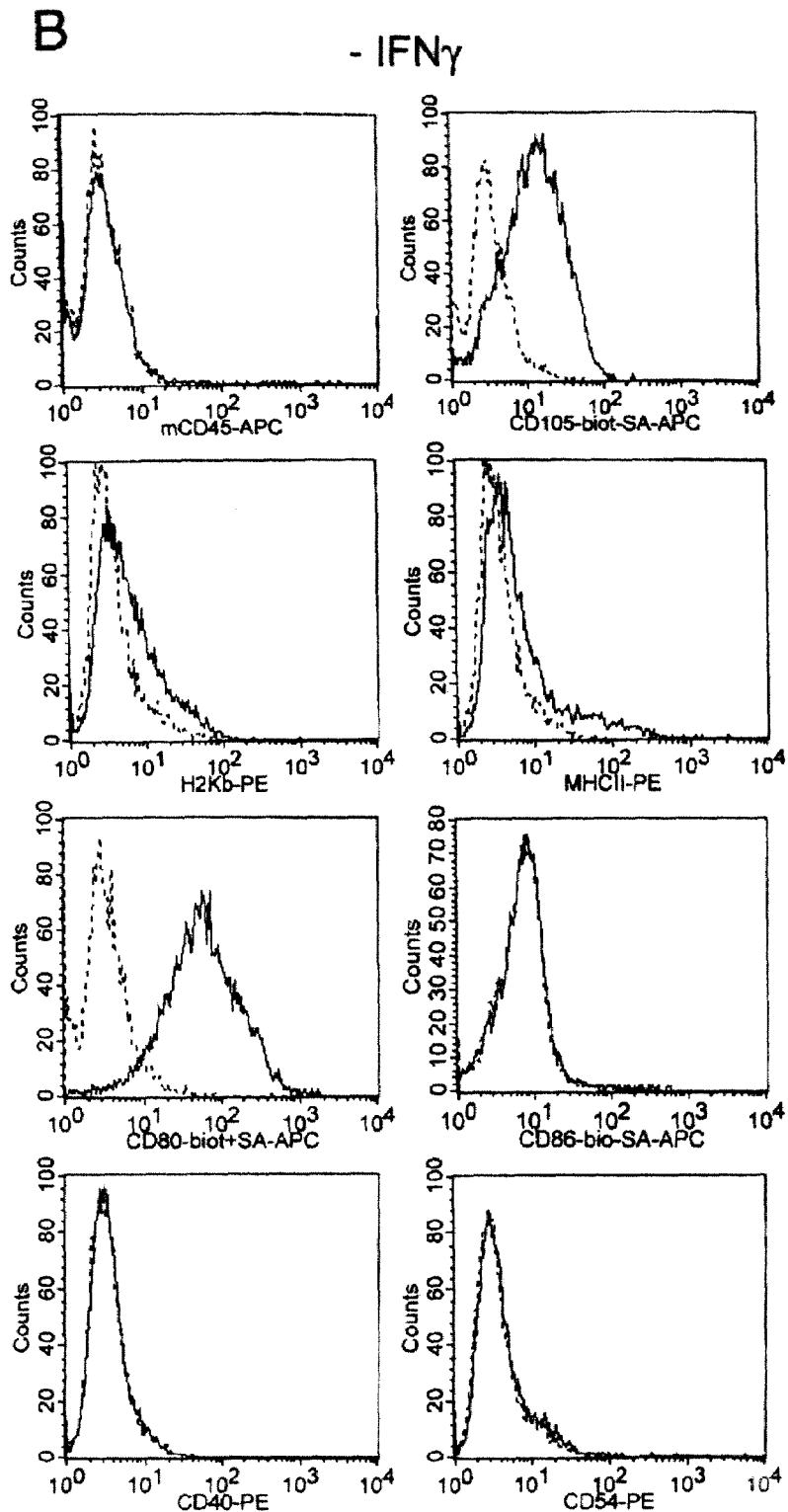
FIG. 1 is a flow cytometry analysis of C57BL/6-derived MSCs. (A) Primary MSCs were isolated from the femurs and tibias of C57BL/6 female mice, culture expanded in DMEM 10% FBS and differentiated along osteogenic and adipogenic lineage cells as described in the methods section. Alizarin Red S was used to stain calcium in the mineralized extracellular matrix and oil-Red was used to stain adipocytic vesicles. Top panels show stained undifferentiated cells. C57BL/6 MSC were analyzed by flow cytometry for CD45, CD105, MHC class I (H2-Kb), MHC class II (I-Ab), CD80, CD86, CD40 and CD54 cell surface expression. Polyclonal MSCs (B), MSCs clone 4 (C), clone 6 (D) and clone 10 (E) were analyzed by flow Where indicated, MSCs were first treated with recombinant mouse IFNγ (50 ng/ml) for 20 hrs prior to flow cytometry analysis. Plots show isotype control IgG staining profile (doted line) versus specific Ab staining profile (thick line)
Figure 1:
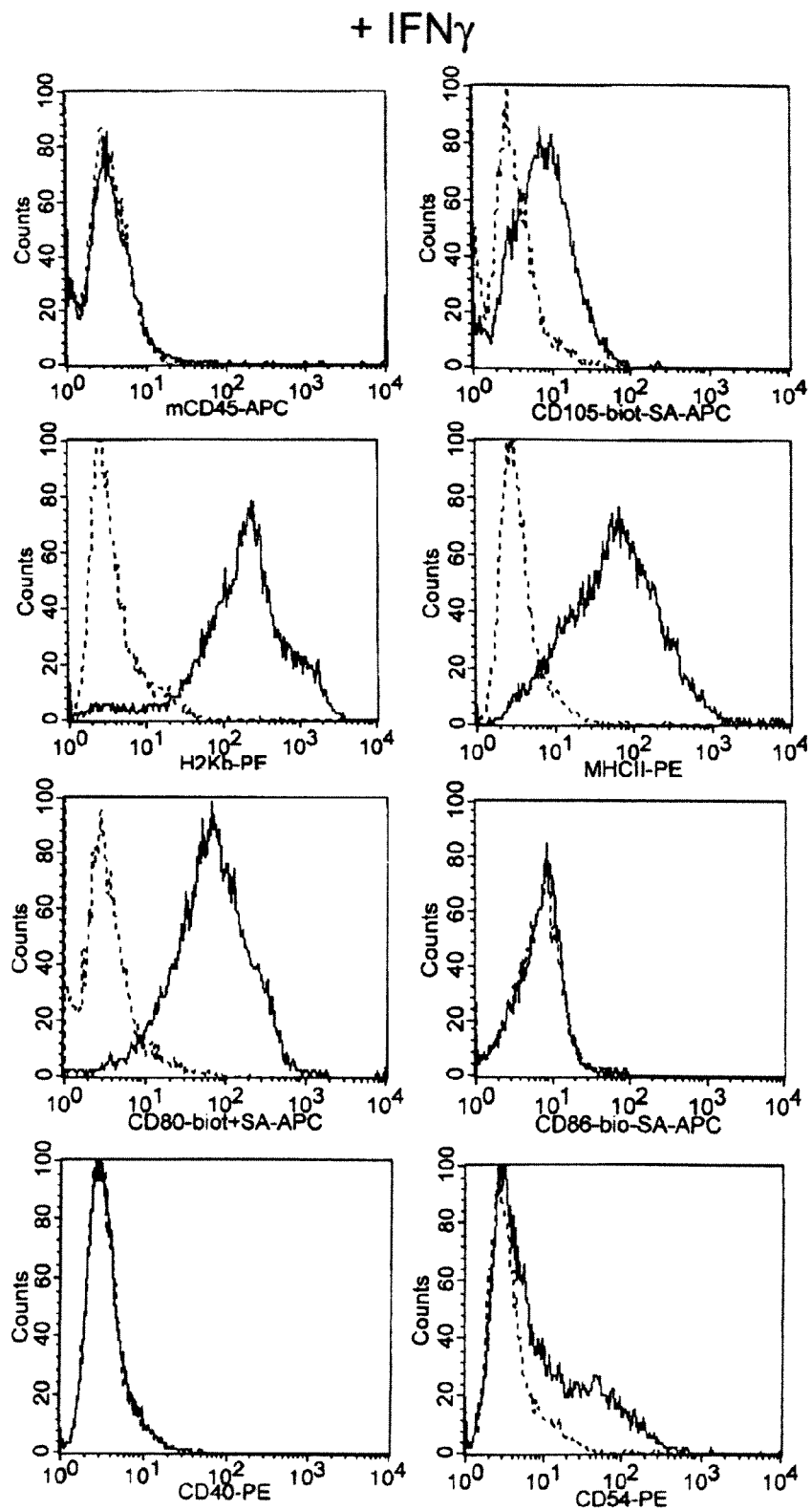
Figure 1C:
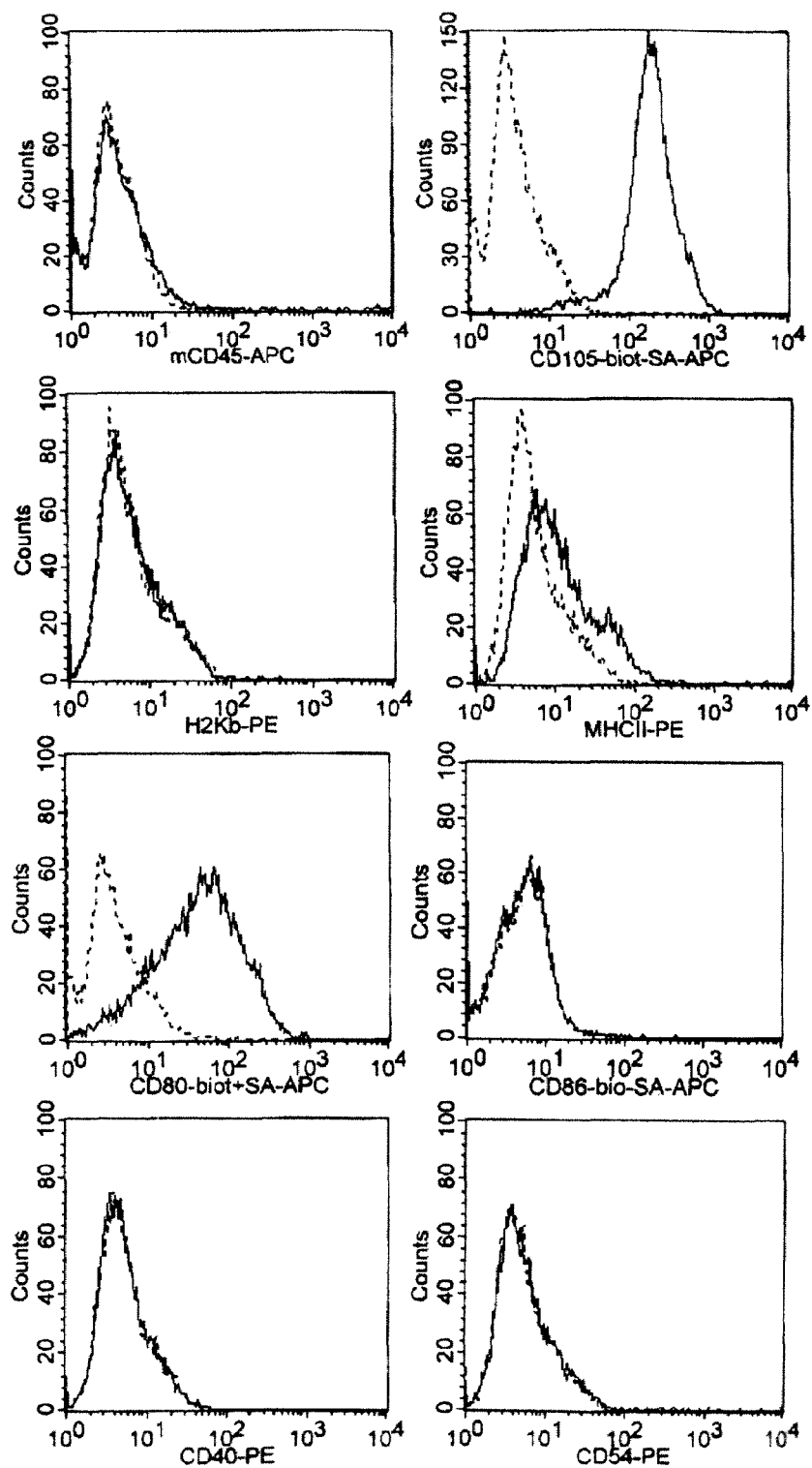
Figure 1:
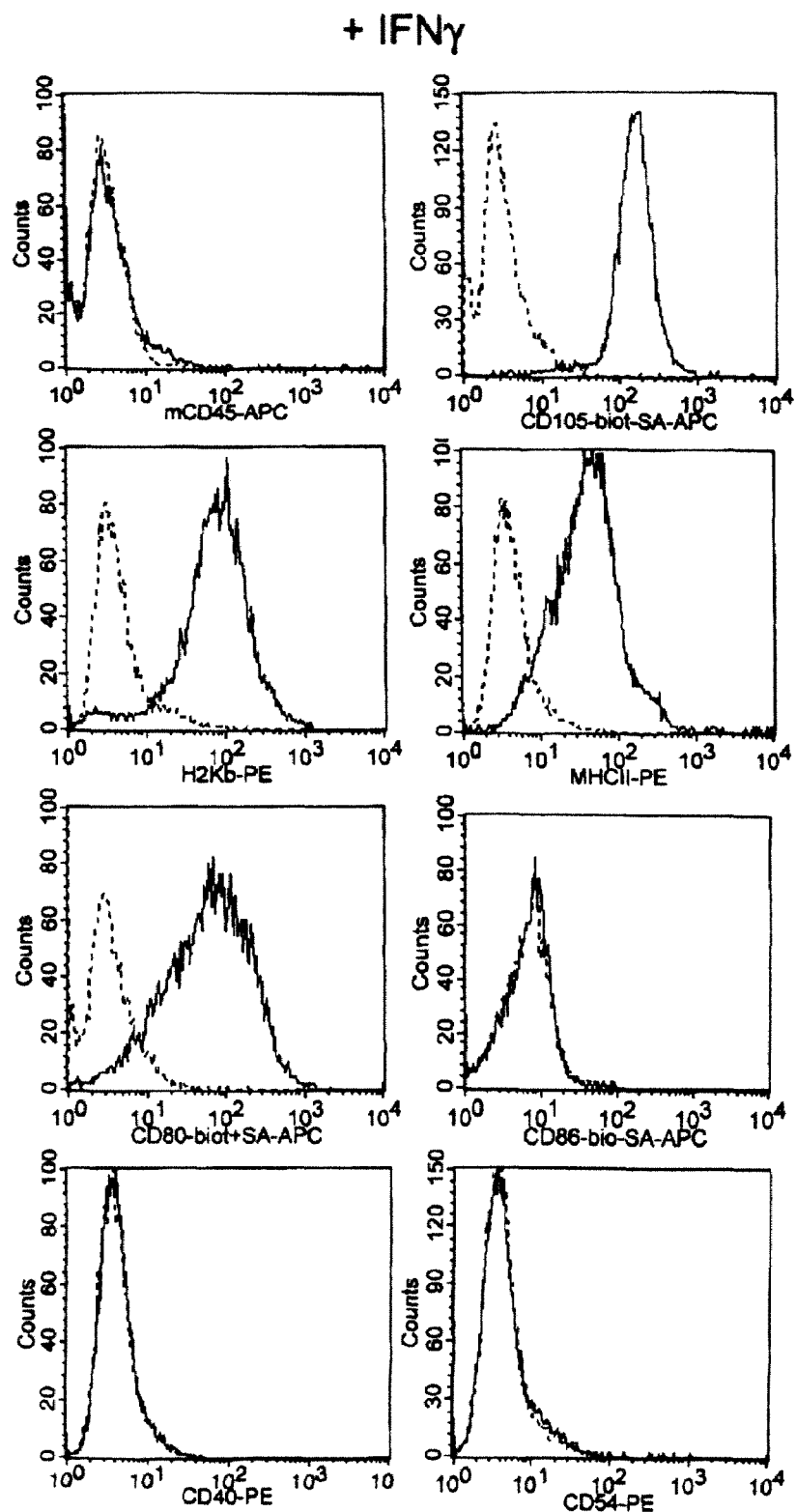
Figure 1:
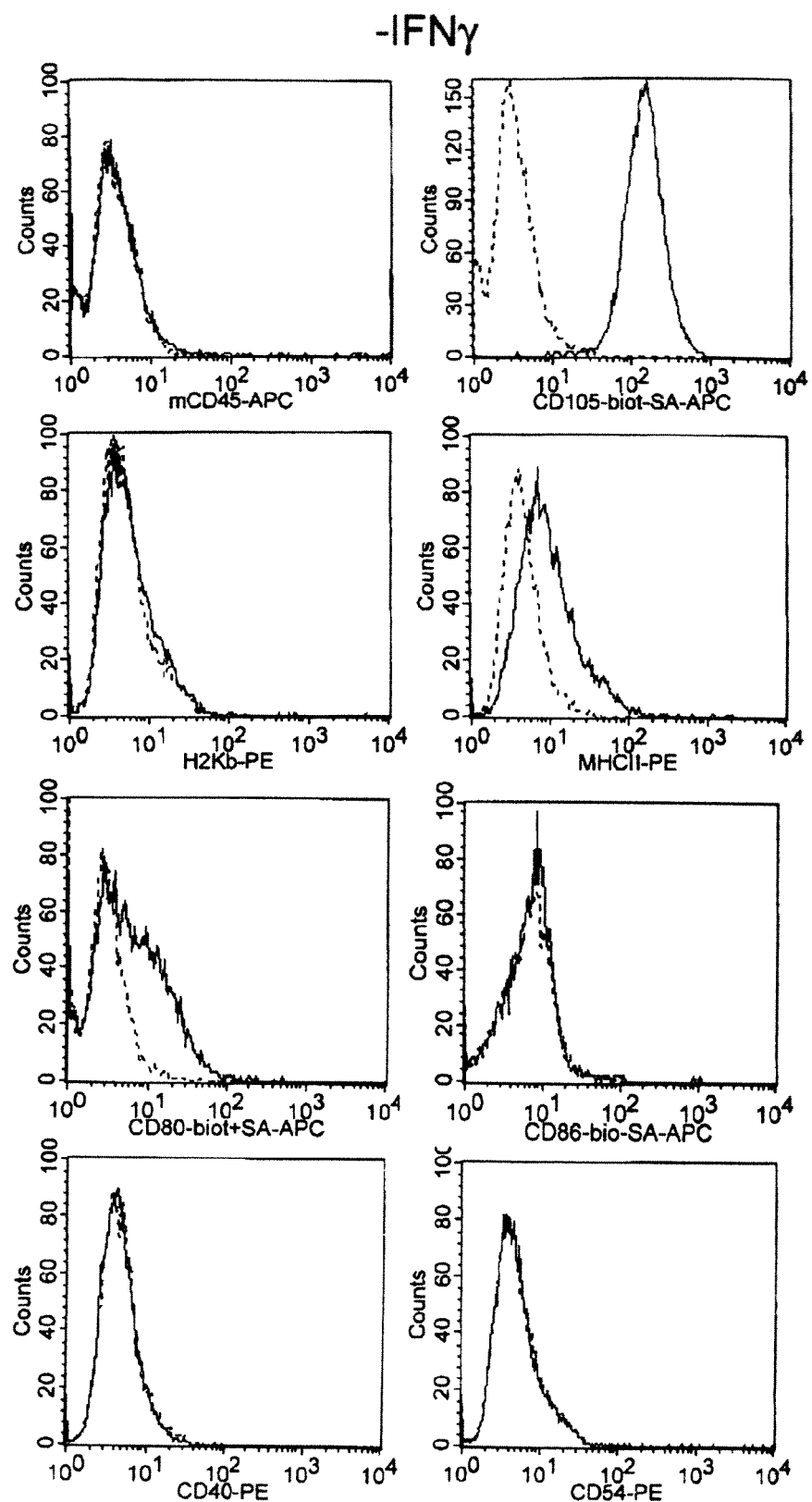
Figure 1:
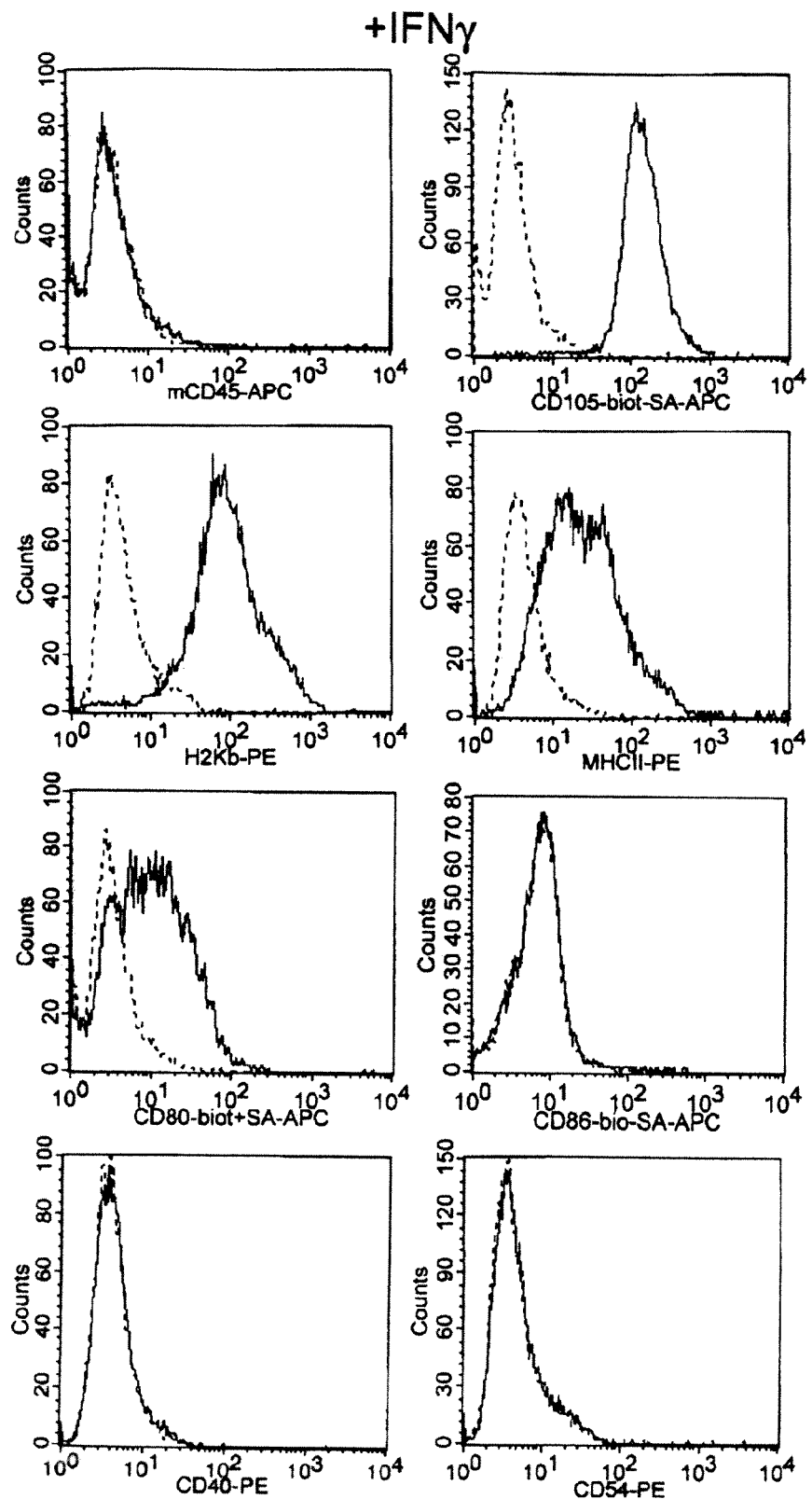
Figure 1:
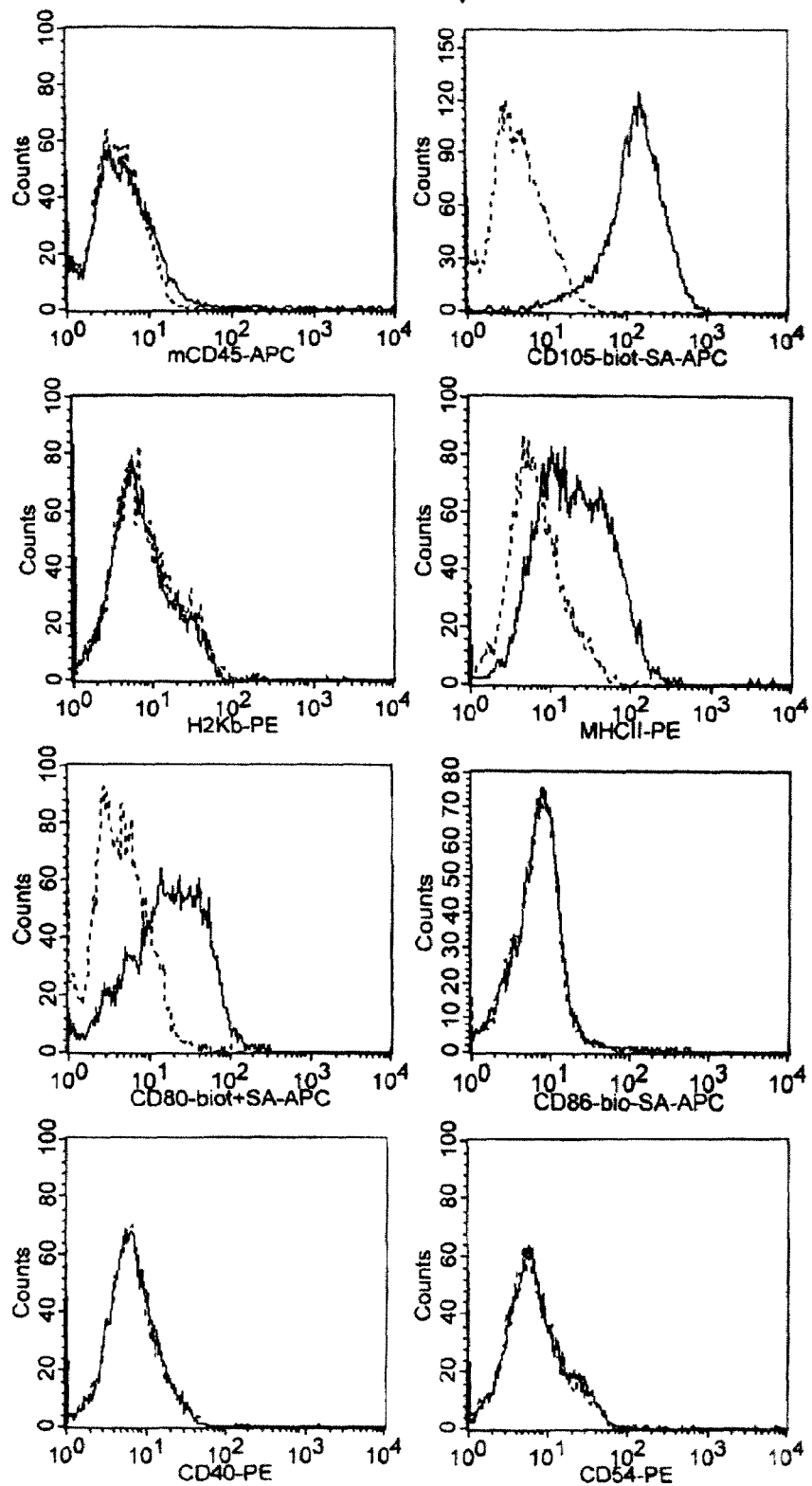
Figure 1:
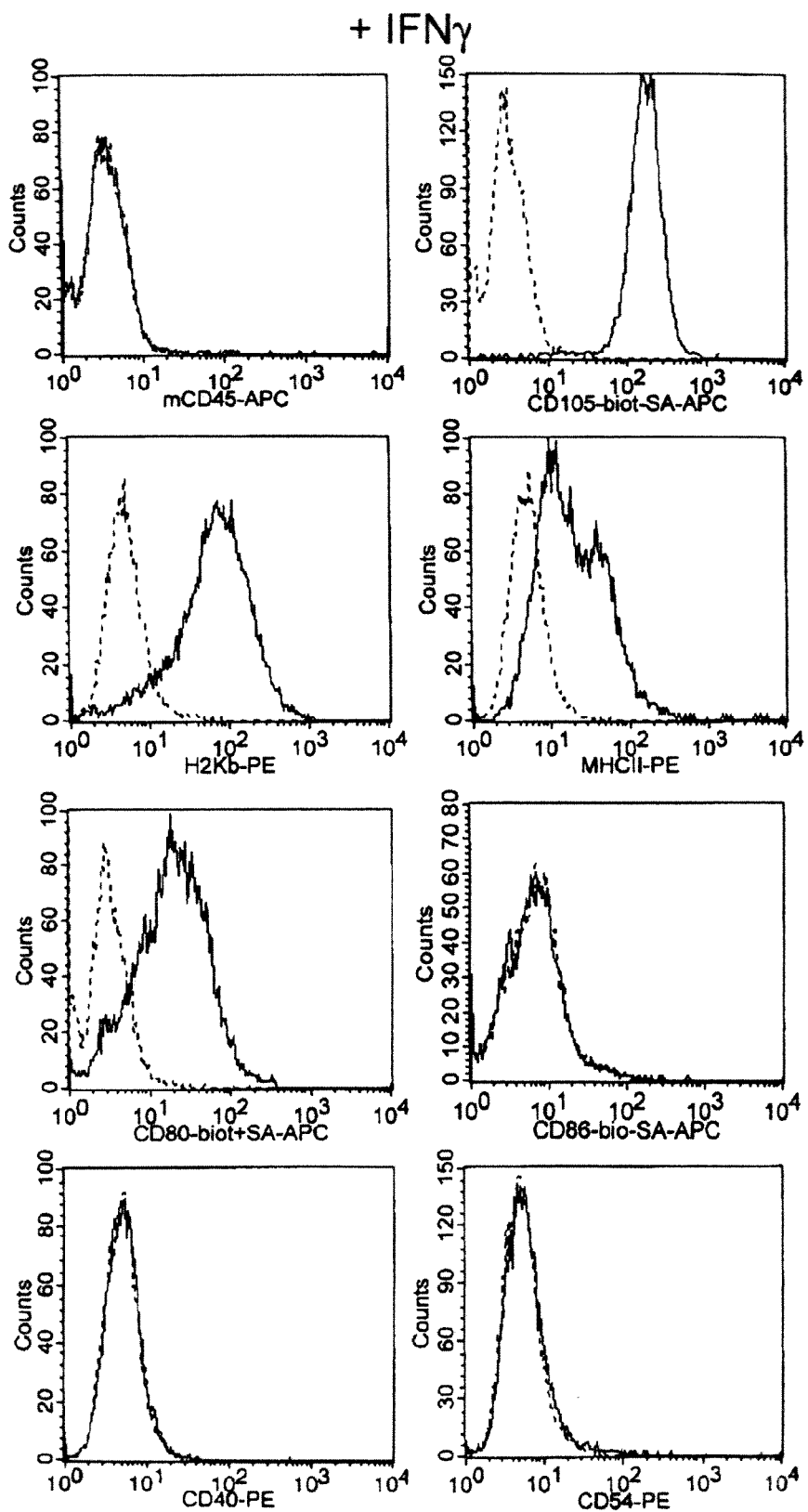

The present invention relates to novel antigen-presenting cells and their use in modulation of immune responses.

Marrow stromal cells (MSCs) under specific culture conditions, can differentiate along multiple cell lineages, including adipocytes, chondrocytes, osteocytes, myocytes, astrocytes, neurons, endothelial cells and lung epithelial cells. Since no single surface marker has been described for purification, MSCs are generally isolated based on their adherence to tissue culture plates, resulting in a semi-homogenous population characterized by the absence of hematopoietic and endothelial surface markers such as CD45 and CD31, and by the expression of CD105, CD73 and CD44.

Stromal cells are known to exhibit immune suppressive properties. However, in accordance to the present invention it has been surprisingly discovered that stromal cells have antigen-presenting properties when stimulated by interferonγ (IFNγ). Thus, there is provided novel antigen-presenting cells that are stromal in origin.

The antigen-presenting cells of the present invention are stromal cells preferably of bone marrow origin and as such can be obtained from bones such as femurs or tibias. However stromal cells can also originate from other tissues such as but not limited to blood and skin. In one embodiment, stromal cells can be obtained by plating whole marrow from femurs and tibias such as to isolate cells that can adhere to the plates. Preferably, the cells are cultured until a homogenous population is obtained. Clones of the stromal cells can also be obtained by limiting dilution of polyclonal populations.

The stromal antigen-presenting cells of the present invention can process and display an antigen in association with MHC II determinant that is recognized by T cells. For example, IFNγ stimulated stromal cells that have been pulsed with an antigen and contacted with T cells are capable of inducing the production of IL-2. The antigen presenting cells of the present invention can therefore be used to stimulate or generate an immune response. It will be appreciated that by stimulate or generate it is meant that the immune response can be triggered or that the response can be modulated by the stromal antigen-presenting cells. In one embodiment, an antigen is incubated over an appropriate period of time with stromal cells that have been IFNγ stimulated and administered in an animal. The time of incubation with the antigen that is needed to produce stromal cells capable of generating an immune response may depend on the antigen. In a preferred embodiment the incubation time is 12 and 24 hours.

In one embodiment, incubation of stromal cells with IFNγ induces the expression of the B7-H1 molecule therefore providing isolated stromal cells that can be used to modulate the immune response of an animal.

While the stimulation of the stromal cells requires IFNγ, it will be appreciated that other adjuvant may be used to modulate the effectiveness of antigen presentation: by stromal cells. Such adjuvants may comprise cytokines and chemokines, including but not restricted to IL-1, IL-2, IL-3, IL-4, IL-5, IL-6, IL-7, IL-10, IL-12, IL-15, IL-18, IL-21, IL-23, TNF-alpha, Lymphotactin, Flt3L, PGE-2, SLC, MIP-1, CXCL1, DC-CK1, bacteria and/or viruses or extracts thereof, including but not restricted to Cholera Toxin, enterotoxin, LPS, lypoglycans, hepatitis non-structural proteins, lipooligosaccharide, BCG, BCG-CWS, virosomes, mannoproteins, proteoliposomes, outer-membrane protein A; Chaperone-rich cell lysates fractions; Heat-shock proteins (HSP) and HSP fusion proteins; Uric Acid; CpG oligodeoxynucleotides; Thermal and/or mechanical stress; Toll-like receptors activators; Protein-bound polysaccharide K (PSK); Piceatannol, Tumor cells fused to marrow stromal cells; Freud's adjuvant and derivatives; Alum's adjuvant and derivatives; RNAs and small-interfering RNAs; Stressed, apoptotic or necrotic tumor cells; Biodegradable biospheres, including but not restricted to PLGA and derivatives, liposomes, mannosylated liposomes, cell-derived exosomes; Latex or polystyrene particles; Antibodies; Biological response modifiers, including but not restricted to OK-432; Pathogen-mimicking nanoparticles; Alpha-tocopheryl succinate; CEA; Listeriolysin O; Antibody surface-modified microparticles; Synthetic pseudodipeptide, including but not restricted to OM-197; Nontoxic chimeric enterotoxin (mCTA/LTB). These adjuvants may be used for in vitro stimulation of stromal cells but may also be incorporated as part of compositions comprising stromal antigen-presenting cells of the present invention for in vivo modulation of an immune response.

In general, antigens that can be processed by antigen presenting cells are well known in the art. Proteins, lipids, carbohydrates, glycoproteins, nucleic acids and fragments thereof and the like may therefore be processed to be presented by stromal cells.

Activated stromal cells that have been pulsed with an antigen may be provided to an animal to generate an immunogenic response to the antigen. For example, the exposure of IFNγ stimulated stromal cells to tumor antigens can prevent or retard the development of tumors expressing the antigen when the stimulated stromal cells are injected in an animal. Similarly activated stromal cells pulsed with infectious organisms antigens may also be used to protect against, for example, bacterial, mycobacterial, viral infections as well as infections from unicellular and pluricellular eukaryotes and emerging infectious organisms. Furthermore, the stromal antigen-presenting cells of the invention can be used to modulate the immune response in autoimmune and alloimmune response to native and allogenic antigens.

Therefore, the present invention further provides a therapeutic composition comprising stromal antigen-presenting cells that have been exposed to one or more antigens and a therapeutically acceptable carrier. As used herein, a therapeutically acceptable carrier includes any solvents, including water, dispersion media, culture from cell media, isotonic agents and the like that are non-toxic to the host. Preferably, it is an aqueous isotonic buffered solution with a pH of around 7.0. The use of such media and agents in therapeutic compositions is well known in the art. Except insofar as any conventional media or agent is incompatible with the stromal antigen-presenting cells of the present invention, use of such conventional media or agent in the therapeutic compositions is contemplated. It will also be appreciated that supplementary active ingredients, such as adjuvants (as described above) can also be incorporated into the compositions.

The therapeutic compositions of the present invention may be administered to an animal in need thereof. Accordingly, the present invention provides methods for inducing an immune response in an animal in need of such response, which comprise administering to an animal an immunologically effective amount of the stromal antigen-presenting cells of the invention that have been pulsed with an antigen. The present invention also provides methods for preventing or treating a tumor in an animal, which comprise administering to an animal an anti-tumor effective amount of the stromal antigen-presenting cells of the invention.

Determination of an animal is in "need thereof" of the cells of the present invention can be determined by those skilled in the art for example by screening a patient with conventional methods for the presence of cancer, or by identifying bacterial strains responsible for an infection. Similarly, an amount of antigen-presenting cells of the present invention that is immunologically effective can be determined by the person skilled in the art such as a physician.

The term "animal" used herein encompasses all mammals, including human. Preferably, the animal of the present invention is a human subject.

The tumors contemplated by the present invention, against which the immune response is induced, or which is to be prevented or treated, may include but are not limited to melanoma, lymphoma, plasmocytoma, sarcoma, glioma, thymoma, leukemias, breast cancer, prostate cancer, colon cancer, esophageal cancer, brain cancer, lung cancer, ovary cancer, cervical cancer, hepatoma, and other neoplasms known in the art.

The immune response induced in the animal by administering the subject stromal antigen-presenting cells of the invention may include cellular immune responses mediated primarily by cytotoxic T cells, capable of killing tumor cells, as well as humoral immune responses mediated primarily by helper T cells, capable of activating B cells thus leading to antibody production. The type of response can be assessed by techniques that are known in the art and knowledge of the type of response may advantageously be used to modulate the response.

The terms "an immunologically effective amount", "an anti-tumor effective amount", or "an tumor-inhibiting effective amount" refer to the amount of the stromal antigen-presenting cells to be administered to achieve the desired effect. This amount can be determined by a physician with consideration of individual differences in age, weight, tumor size, extent of infection or metastasis, and condition of the patient.

The administration of the compositions of the present invention may be carried out in any convenient manner, including by aerosol inhalation, injection, ingestion, transfusion, implantation or transplantation. Preferably, the stromal antigen-presenting cells of the present invention are administered to a patient by subcutaneous (s.c.), intraperitoneal (i.p.), intra-arterial (i.a.), or intravenous (i.v.) injection. The therapeutically acceptable carrier should be sterilized by techniques known to those skilled in the art.

In a further embodiment of the invention the stromal antigen presenting cells can be included in a vaccine composition. The vaccine composition of the present invention can be administered via various routes including oral, subcutaneous, intravenous, and intramuscular introduction. However, it should be understood that the amount of the active ingredient actually administered ought to be determined in light of various relevant factors including the condition to be treated, the chosen route of administration, the age, sex, and body weight of the individual patient, and the severity of the patient's symptom. Therefore, the above does not limit the scope of the invention in any way.

EXAMPLES

Results:

Phenotypic Characterization of Primary MSCs

Primary MSCs were isolated from the femurs and tibias of C57BL/6 mice as previously described (Stagg et al. Hum Gene Ther. 2004 June; 15(6):597-608; Eliopoulos et al. Mol Ther. 2004 October; 10(4):741-8, incorporated herein by reference). Cultured in differentiation media, MSCs were able to give rise to osteogenic and adipogenic cells (FIG. 1A). Phenotypically, MSCs were negative for CD45, CD54, CD86 and CD40 expression and were positive for CD105, MHC class I (H-2 Kb) and CD80 expression as determined by flow cytometry (FIG. 1). When exposed to recombinant mouse IFNγ (50 ng/ml) for 20 hours, MSCs upregulated MHC class I, MHC class II and CD54, but not CD80, while they remained negative for CD86, CD40, and CD45 expression (FIG. 1B).

Immunosuppressive Effects of MSCs

Figure 2:
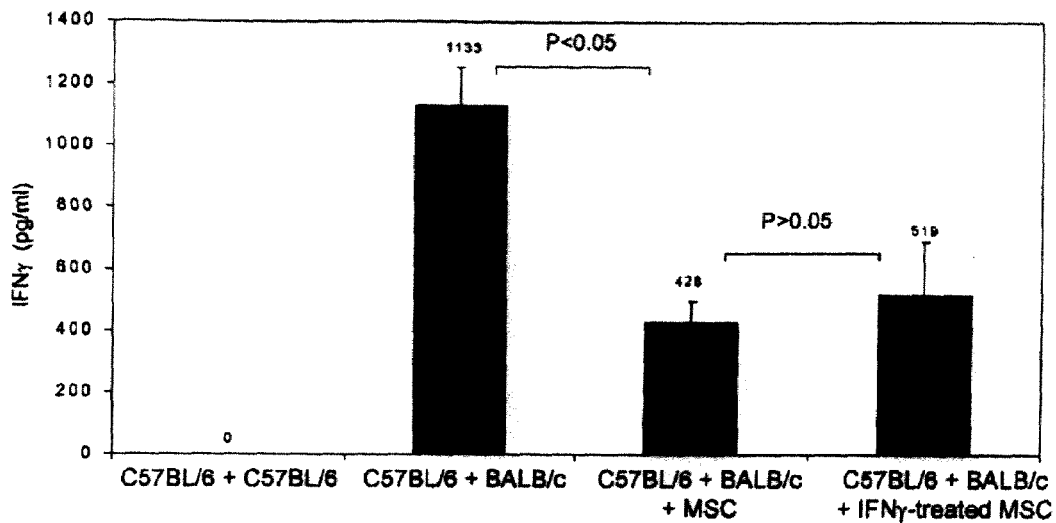
FIG. 2 shows the effect of MSCs on allogeneic and syngeneic immune responses. (A) Two-way mixed lymphocytes reactions were performed with $10^5$ C57BL/6 splenocytes and $10^5$ BALB/c splenocytes in the presence or absence of $10^5$ C57BL/6 naïve or IFNγ-treated MSCs. After 3 days, supernatant was collected and tested for IFNγ release by ELISA (Means of triplicates±standard deviations are shown). (B) DC2.4 cells ($5\times10^4$ cells) were cocultured for 20 hrs with ovalbumin-specific MHC class II-restricted T-T hybridomas (MF2.2D9; $10^5$ cells) in the presence or not of 2.5 mg/ml soluble ovalbumin. Where indicated, $5\times10^4$ naïve or IFNγ-pretreated MSCs were added to the cocultures. After 20 hrs, supernatant was collected and tested for IL-2 release by ELISA (Means of triplicates±standard deviations are shown). (C) Same as (B) and where indicated conditioned supernatant from naïve or IFNγ-treated MSCs were added to the cocultures in replacement of MSCs (Means of triplicates±standard deviations are shown). (D) Same as (B) and where indicated $5\times10^4$ naïve or IFNγ-pretreated paraformaldehyde-fixed MSCs were added to the cocultures in replacement of live MSCs. Alternatively, DC2.4 cells were first pulsed with soluble ovalbumin for 20 hrs and then cocultured with the indicated cells for another 20 hrs (Means of triplicates±standard deviations are shown)
Figure 2:
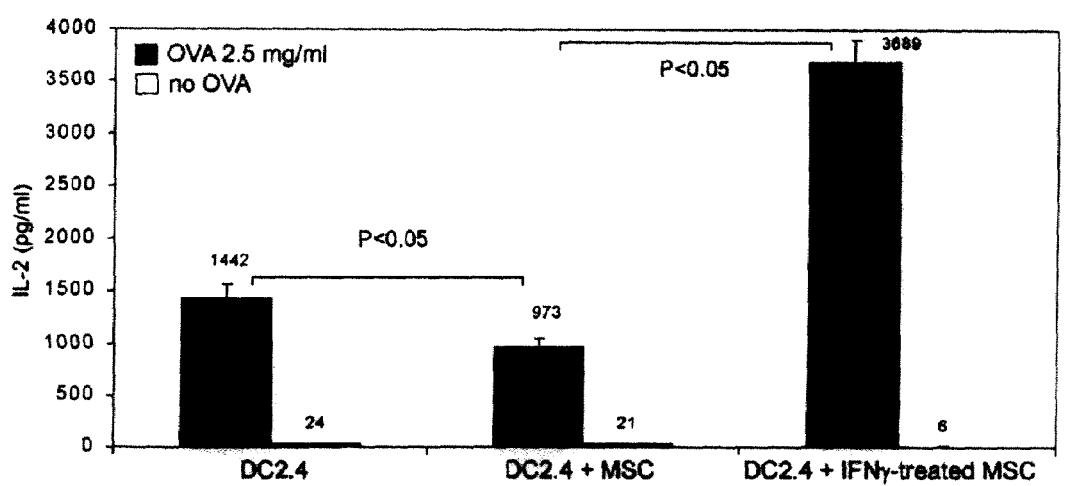
Figure 2:
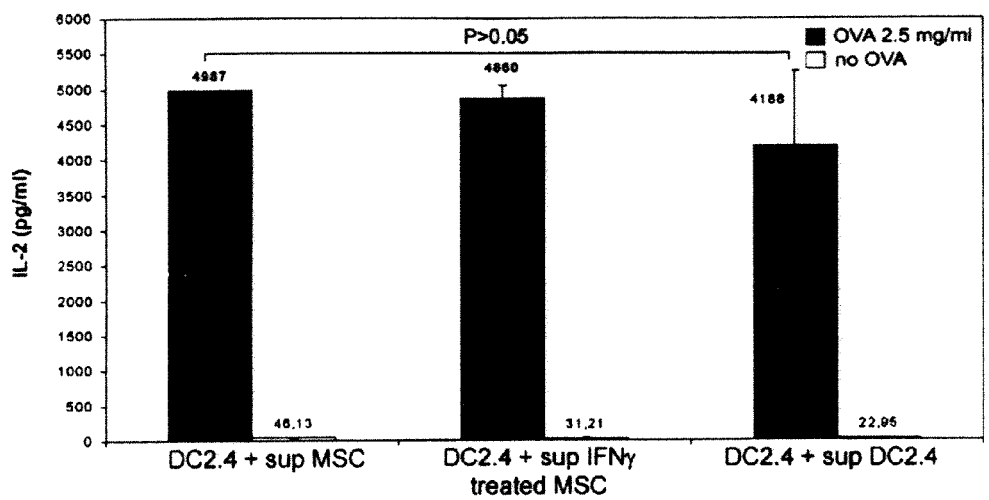
Figure 2:
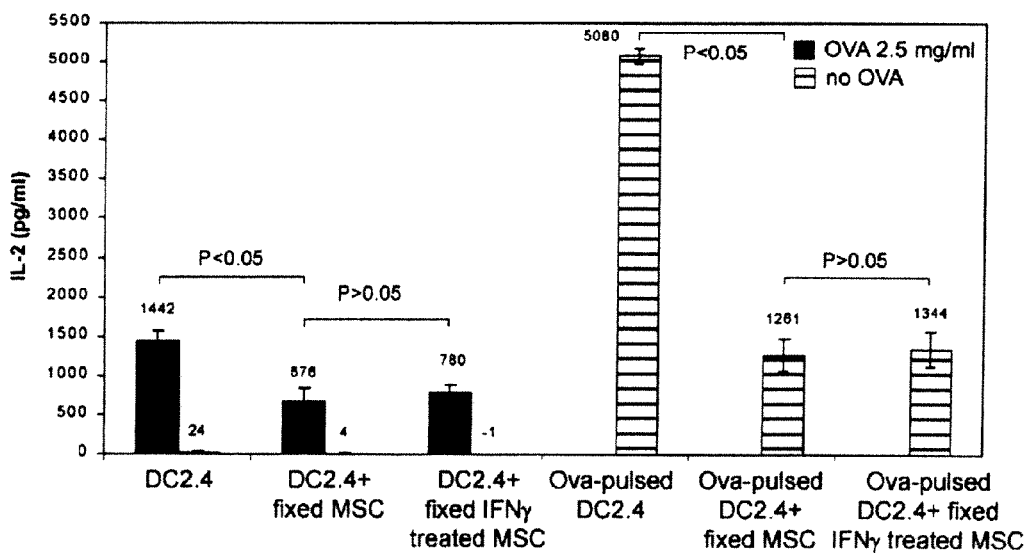

We first evaluated the immunosuppressive effect of C57BL/6-derived mouse MSCs on allogeneic mixed lymphocytes cultures. In accordance with previous studies (Krampera et al. Blood. 2003 May 1; 101(9):3722-9, incorporated herein by reference), the addition of MSCs to allogeneic cocultures of C57BL/6 and BALB/c splenocytes significantly inhibited the activation levels of the cocultures (P<0.05 by T-test; FIG. 2A). Also consistent with previous studies (Le Blanc et al. Exp Hematol. 2003 October; 31(10):890-6), prestimulation of MSCs with recombinant IFNγ did not hinder their allogeneic immunosuppressive effect (P>0.05 by T-test; FIG. 2A).

In order to test whether MSCs could suppress syngeneic immune responses, we used a well-described ovalbumin-specific T-T hybridoma assay (Shen et al. J Immunol. 1997 Mar. 15; 158(6):2723-30, incorporated herein by reference). In this assay, immortalized dendritic cells (DC2.4 cells) are cocultured for 20 hours with syngeneic MHC class II restricted ovalbumin-specific T-T hybridomas (MF2.2D9 cells) in the presence of increasing doses of soluble ovalbumin. Twenty hours later, antigen-specific T cell activation is assessed by measuring the level of IL-2 released in the supernatant. When soluble ovalbumin was added to DC2.4 and MF2.2D9 cocultures, significant levels of IL-2 were produced in an antigen dose-dependent manner as determined by ELISA (FIG. 2B). The addition of MSCs to these cocultures significantly inhibited IL-2 release (P<0.05 by T-test, performed twice; FIG. 2B). However, in marked contrast with the allogeneic mixed lymphocytes reaction (FIG. 2A), the addition of IFNγ-treated MSCs to the syngeneic cocultures enhanced IL-2 release (P<0.05 by T-test; FIG. 2B). Since IFNγ did not, on its own, induce MSCs to release IL-2, this suggested that IFNγ modulated mouse MSCs to become permissive to syngeneic T cell activation.

We thus performed experiments in order to assess the nature of this permissiveness. Specifically, we wanted to determine IFNγ-treated MSCs enhanced or failed to suppress DC2.4-mediated antigen presentation. Firstly, we assessed the effect of conditioned supernatant from naïve or IFNγ-treated MSCs on DC2.4-mediated antigen presentation. As shown in FIG. 2C, conditioned supernatant from naïve or IFNγ-treated MSCs had no significant effect on DC2.4-mediated antigen presentation (P>0.05 by T-test). This suggested that: 1) IFNγ-treated MSCs do not stimulate DC2.4 through a secreted factor, and 2) the suppressive effect of naïve MSCs on syngeneic antigen presentation is independent of a secreted factor. Secondly, we tested whether naïve or IFNγ-treated MSCs modulated DC2.4 in a contact-dependent manner. As shown in FIG. 2D, paraformaldehyde fixed naïve as well as IFNγ-treated MSCs significantly suppressed DC2.4-mediated antigen presentation (P<0.05 by T-test). This suppressive effect was even more pronounced when DC2.4 cells were first pulsed with soluble ovalbumin for 20 hours and then cocultured with fixed MSCs and live hybridoma cells. Taken together, our data suggested that:

1) the suppressive effect of MSCs on syngeneic DC2.4-mediated antigen presentation is contact-dependent, 2) IFNγ treatment of MSCs does not alter their suppressive effect on DC2.4-mediated antigen presentation, and 3) despite their suppressive effect, IFNγ-treated MSCs are permissive to syngeneic antigen presentation. Given these results, we hypothesized that IFNγ induced MSCs to acquire antigen-presenting functions.

Activation of MHC Class II-Restricted Hybridomas by IFNγ-Treated MSCs

Figure 3:
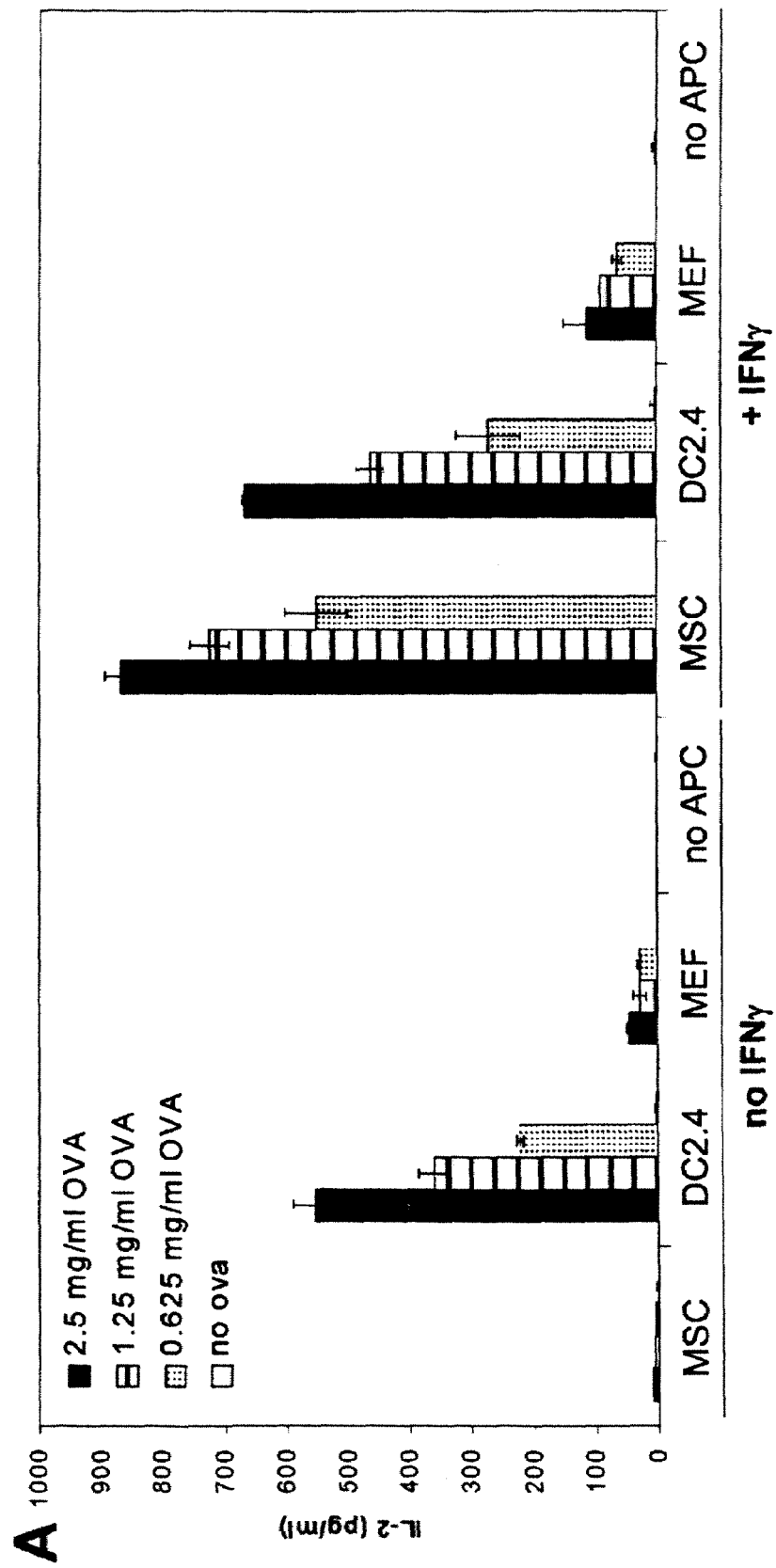
FIG. 3 shows the MSCs-mediated activation of ovalbumin-specific T-T hybridomas (A) C57BL/6 MSCs, DC2.4 or MEF ($5\times10^4$ cells) were cocultured for 20 hrs with ovalbumin-specific MHC class II-restricted T-T hybridomas (MF2.2D9; $10^5$ cells) in the presence of increasing doses of soluble ovalbumin. Where indicated, recombinant mouse IFNγ (50 ng/ml final) was added to the cocultures. After 20 hrs, supernatant was collected and tested for IL-2 release by ELISA (Means of triplicates±standard deviations are shown of one of five experiments). (B) Same as (A), except that clonal MSCs obtained by limiting dilution from the initial preparation were used. (C) Same as (A), except that distinct polyclonal C57BL/6-derived MSCs preparations were used.
Figure 3:
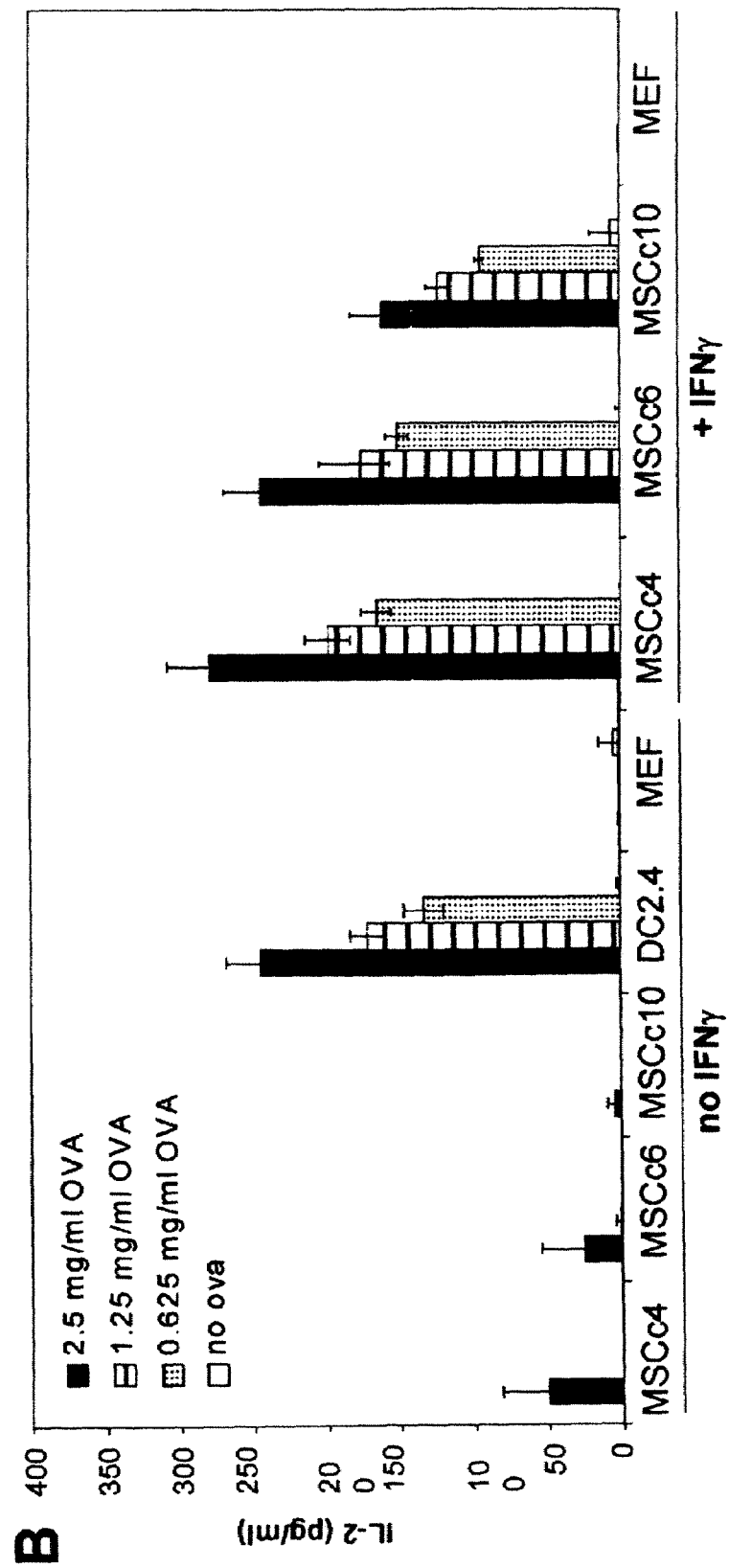
Figure 3:
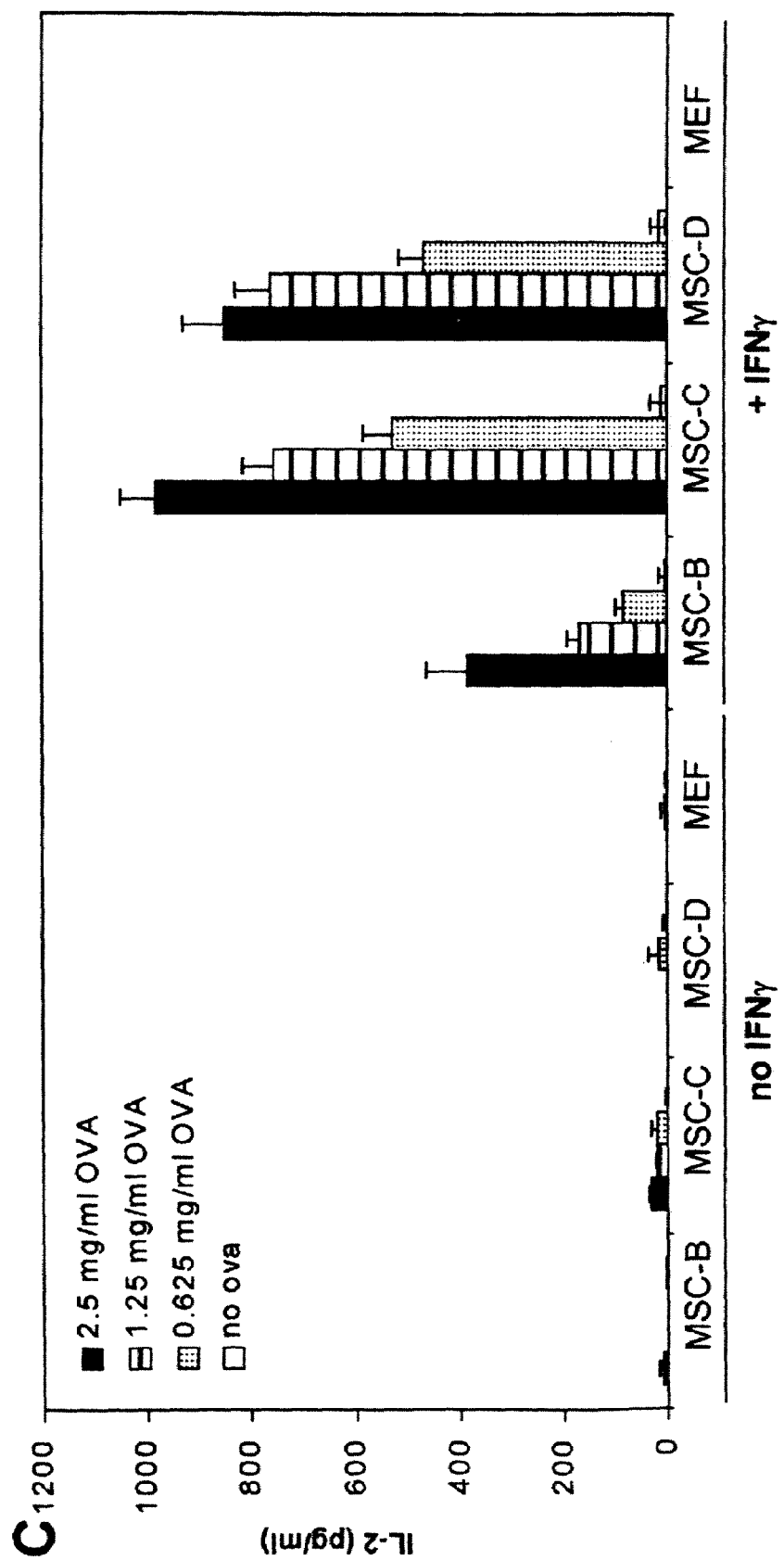

In order to investigate whether IFNγ-treated MSCs could behave as syngeneic antigen presenting cells, soluble ovalbumin was added at increasing doses to cocultures of IFNγ-treated MSCs and MHC class II restricted ovalbumin-specific T-T hybridoma cells. When IFNγ-treated MSCs were exposed to soluble ovalbumin at doses of 2.5, 1.25 and 0.625 mg/ml and cocultured for 20 hours with class II restricted hybridomas, significant levels of IL-2 was detected in the supernatants as measured by ELISA (respectively 867, 722 and 551 pg/ml of IL-2; FIG. 3A). On the other hand, unstimulated MSCs failed to induce IL-2 release in identical conditions. IL-2 levels were below sensitivity (<2 pg/ml) when IFNγ-treated MSCs were cocultured with hybridomas without ovalbumin, or when the hybridomas were cultured with ovalbumin without MSCs. Remarkably, the levels of MHC class II activation induced by IFNγ-treated MSCs were comparable or slightly superior to those obtained with the dendritic cell line DC2.4 (FIG. 3A). This experiment was performed 5 times, each in triplicates, with similar results.

In order to rule out the possibility that the observed MSCs-mediated antigen presentation was the result of an idiosyncratic effect, distinct clonal (FIG. 3B) and polyclonal (FIG. 3C) populations of C57BL/6-derived MSCs were tested with comparable results. Phenotypically, the distinct MSCs populations were very similar (FIG. 1 C,D,E), with the exception of MSC clone 10 that constitutively expressed MHC class II and failed to upregulate MHC class II upon IFNγ treatment.

Figure 4:
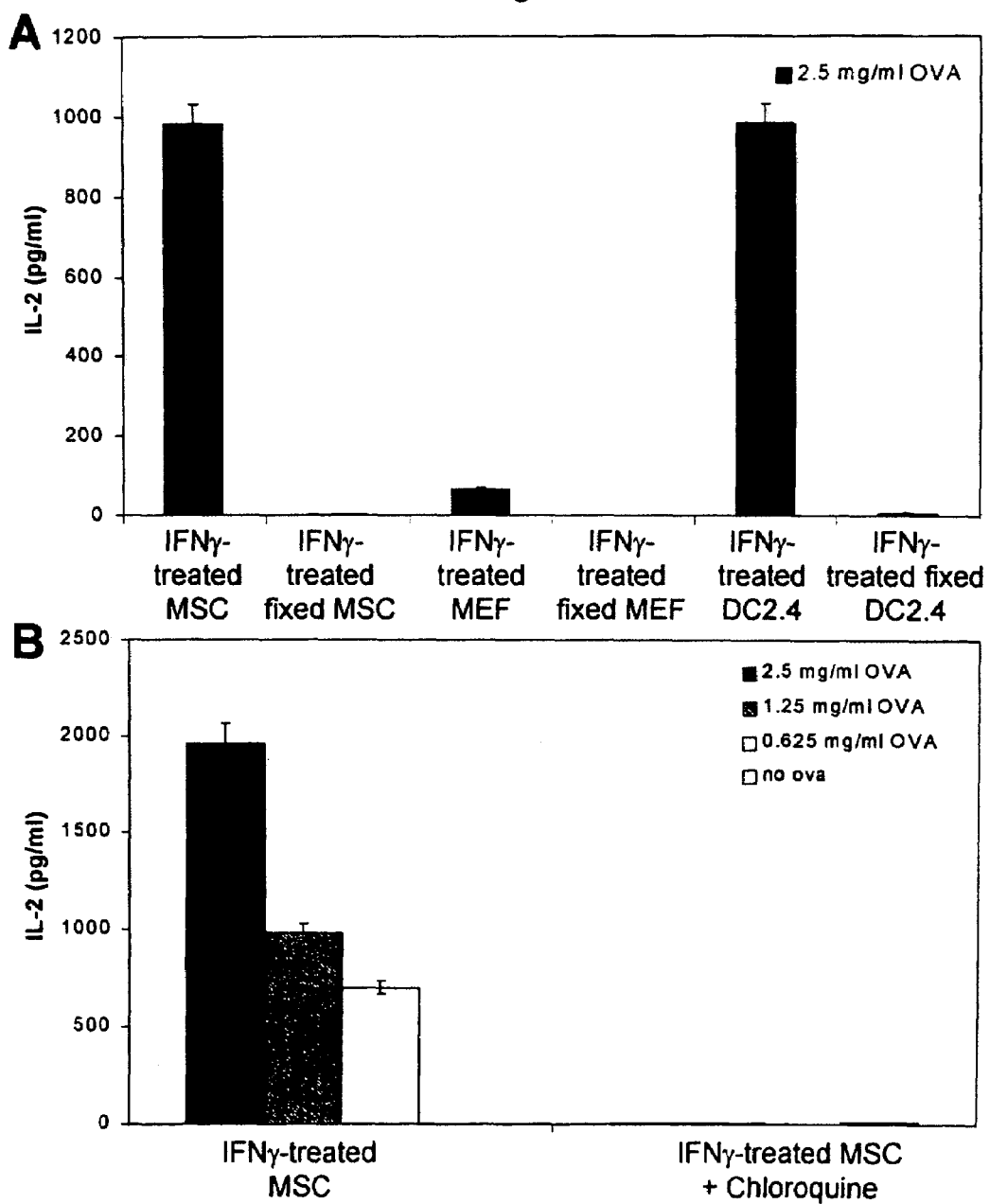
FIG. 4 describes results of Antigen processing for MSCs-mediated antigen presentation. (A) C57BL/6 MSCs, DC2.4 or MEF ($5\times10^4$ cells) were cocultured for 20 hrs with ovalbumin-specific MHC class II-restricted T-T hybridomas (MF2.2D9; $10^5$ cells) in the presence of 2.5 mg/ml of soluble ovalbumin. Where indicated, MSCs were treated with IFNγ (50 ng/ml final). Where indicated, MSCs were first fixed with paraformaldehyde prior to coculture. After 20 hrs, supernatant was collected and tested for IL-2 release by ELISA (Means of triplicates±standard deviations are shown). (B) MSCs ($5\times10^4$ cells) were cocultured for 20 hrs with MF2.2D9 cells ($10^5$ cells) in the presence of increasing doses of soluble ovalbumin. Where indicated, MSCs were treated with chloroquine (100 μM) 30 min prior to and during antigen exposure.

Our data suggested at this point that mouse MSCs can process ovalbumin into MHC class II restricted peptides and activate ovalbumin-specific T-T hybridomas. To exclude the possibility that free peptides in the ovalbumin preparation could have mediated antigen presentation in the absence of antigen processing as others have reported (Reis e Sousa et al. J Exp Med. 1995 Sep. 1; 182(3):841-51), the above-mentioned experiments were repeated using paraformaldehyde pre-fixed MSCs subsequently exposed to ovalbumin. As shown in FIG. 4A, pre-fixed IFNγ-treated MSCs did not induce IL-2 release when cocultured with hybridomas and ovalbumin. This suggested that processing of ovalbumin is required for MSCs-mediated antigen presentation. To assess MSCs processing of ovalbumin was the result of endosomal protein proteolysis as would be expected of a professional APCs (Shen et al. J Immunol. 1997 Mar. 15; 158(6):2723-30), we treated the MSCs with chloroquine. Chloroquine is known to prevent protein hydrolysis by cathepsins by raising the pH in the endosomal and lysosomal compartments (Ohkuma et al. Proc Natl Acad Sci USA. 1978 July; 75(7):3327-31). As shown in FIG. 4B, treatment with chloroquine completely inhibited the presentation of ovalbumin peptides on MHC class II molecules.

CD80-Dependent Activation of OT-II Cells by IFNγ-Treated MSCs

Figure 5:
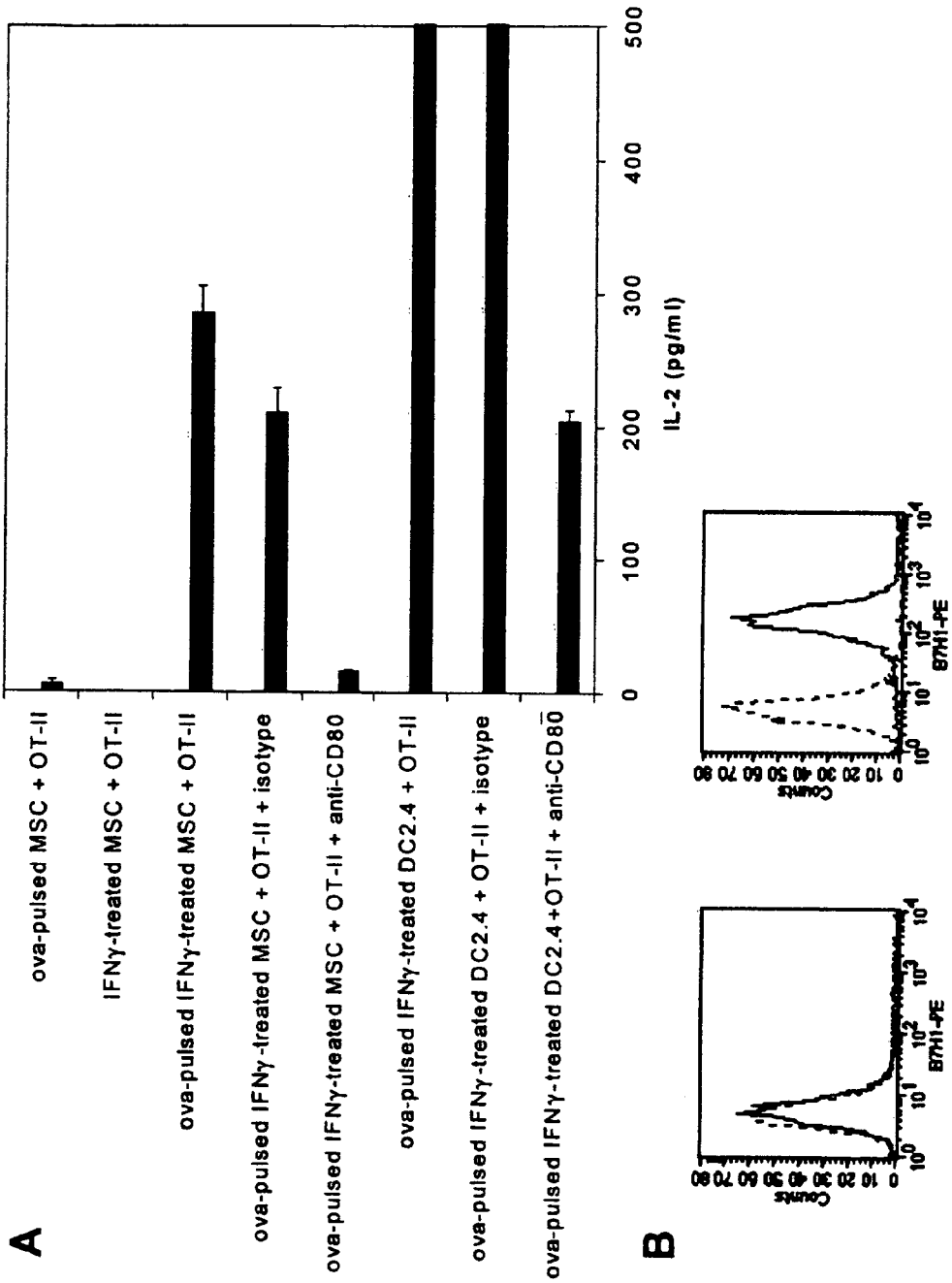
FIG. 5 shows MSCs-mediated activation of primary OT-II CD4+ T cells. (A) C57BL/6 MSCs or DC2.4 were pre-treated with recombinant mouse IFNγ (50 ng/ml) and soluble ovalbumin (2.5 mg/ml) for 20 hrs and then cocultured ($5\times10^4$ cells) for 48 hrs with ovalbumin-specific purified CD4+ T splenocytes ($10^5$ cells; >80% purity) from OT-II transgeneic mice. Where indicated, MSCs and DC2.4 were first incubated with a blocking antibody to mouse CD80 or an isotypic control 30 min prior to and during antigen exposure. After coculture, supernatant was collected and tested for IL-2 release by ELISA (Means of triplicates±standard deviations are shown). (B) C57BL/6 MSCs were analyzed by flow cytometry for B7-H1 surface expression before and after recombinant IFNγ treatment (50 ng/ml for 20 hrs). Plots show isotype control IgG staining profile (doted line) versus specific Ab staining profile (thick line).

We next assessed whether IFNγ-treated mouse MSCs could activate primary transgenic T cells. Ovalbumin-specific CD4+ T cells were isolated from the spleens and lymph nodes of transgenic OT-II mice and purified by negative selection (>80% purity). When purified CD4+ OT-II cells were cocultured for 48 hours with ovalbumin-pulsed IFNγ-treated MSCs, we observed significant levels of IL-2 production (FIG. 5A). We then investigated whether CD80 expression on mouse MSCs was required for OT-II activation. As shown in FIG. 5A, the addition of a blocking antibody to CD80 inhibited the activation of CD4+ OT-II cells as determined by a 90% decrease in IL-2 production compared to isotypic control (P<0.05 by T-test). Taken together, our experiments with ovalbumin-specific hybridomas and ovalbumin-specific primary OT-II cells strongly suggested that mouse MSCs can efficiently process exogenous antigen, present antigenic peptides on MHC class II molecules and activate, mainly in a CD80-dependent manner, ovalbumin-specific T cells.

B7-H1 Expression is Induced on Mouse MSCs Following IFNγ Treatment

We investigated by flow cytometry the expression levels of other costimulatory molecules on naïve and IFNγ-stimulated MSCs. Unstimulated as well as IFNγ-treated mouse MSCs were found to be negative for CD86, CD40, CD28, ICOSL, 41BBL and B7-DC surface expression. However, after IFNγ stimulation, mouse MSCs upregulated surface expression of B7-H1 molecules (FIG. 5b).

MSCs Cannot Induce Antigen Cross-Presentation

We further tested whether mouse MSCs could induce activation of MHC class I restricted hybridomas in response to soluble ovalbumin. This experiment essentially measured the ability of MSCs to induce cross-presentation of exogenous antigens. While DC2.4 cells induced significant antigen cross-presentation as previously shown (Shen et al. J. Immunol. 1997 Mar. 15; 158(6):2723-30), unstimulated and IFNγ-stimulated MSCs could not induced IL-2 release (FIG. 6). In order to determine whether MSCs could still process exogenous ovalbumin into MHC class I-associated peptides without inducing IL-2 production, we performed flow cytometry analysis of ovalbumin-pulsed MSCs using a monoclonal antibody specific for the SIINFEKL/H-$2K^b$ complex (clone 25D1.16, Porgador et al. Immunity. 1997 June; 6(6):715-26, incorporated herein by reference). While the antibody positively labelled IFNγ-treated MSCs pulsed with 10 μM of the synthetic SIINFEKL peptide, unstimulated as well as IFNγ-stimulated MSCs pulsed with soluble ovalbumin were not detected by the antibody. Our results therefore suggested that mouse MSCs cannot perform exogenous antigen cross-presentation via the MHC class I pathway.

Figure 7A:
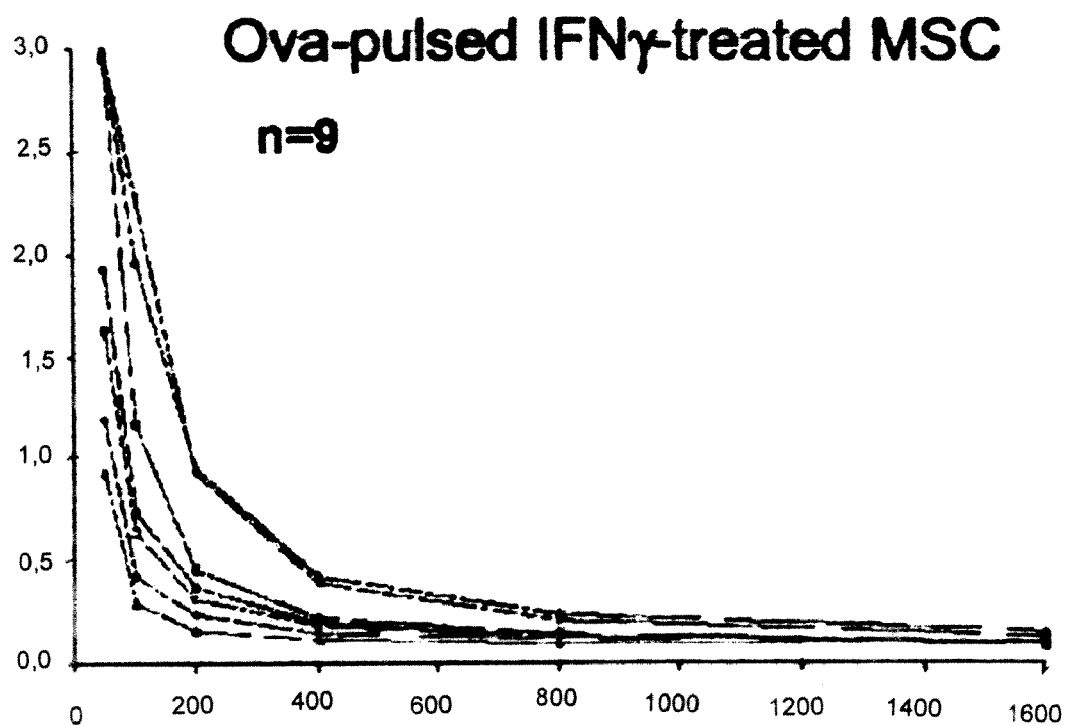
FIG. 7 shows MSCs-induced antigen-specific immune responses in vivo. C57BL/6 MSCs or MEF cells were treated in vitro with recombinant IFNγ and soluble ovalbumin for 20 hrs, washed with PBS and injected ($0.1\times10^6$ cells) intraperitoneally into syngeneic C57BL/6 mice. Two weeks later, the mice were injected a second time with the corresponding cells (0.2×10⁶) and one week after, ovalbumin-specific immune responses were assessed. (A) Serum samples of immunized mice were collected at day 20 after the first immunization, added at different dilutions to ovalbumin-coated 96-well plates and titerred for anti-ovalbumin antibodies. (B) Splenocytes were isolated from immunized mice at day 21 after the first immunization and restimulated in vitro with mitomycin C-treated ovalbumin-expressing E.G7 cells. Five days later, CD8+ T cells were purified from the reactivated splenocytes (>90% purity) and used as effectors in annexin-V-based CTL assays against EL4 or E.G7 target cells. (C) Immunized mice were challenged at day 21 after the first immunization with a subcutaneous injection of 2×10⁶ cells of ovalbumin-expressing E.G7 tumor cells.
Figure 7C:
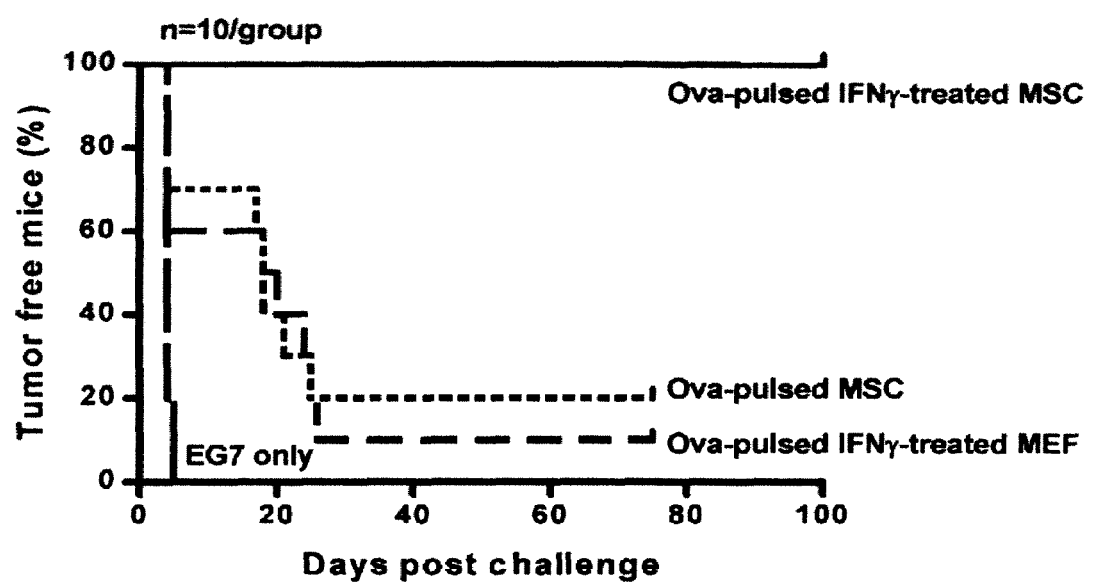

IFNγ-Treated MSCs Pulsed with Soluble Ovalbumin Induced Antigen-Specific Immune Responses In vivo Next, we investigated the ability of IFNγ-treated MSCs to induce antigen-specific immune responses in vivo. Polyclonal MSCs and control MEF (both from C57BL/6 origin) were stimulated with recombinant IFNγ and soluble ovalbumin, IFNγ only or ovalbumin only for 20 hrs, washed with PBS and injected intraperitonealy into syngeneic C57BL/6 mice. Two weeks later, the mice were injected a second time with the corresponding cellular vaccine and one week after, ovalbumin-specific immune responses were assessed. Firstly, we determined whether mice injected with ovalbumin-pulsed IFNγ-treated MSCs could generate anti-ovalbumin antibodies. Although few mice developed anti-ovalbumin antibodies, we observed no significant differences between MSCs injected versus MEF injected mice (FIG. 7A). Secondly, we investigated whether mice injected with ovalbumin-pulsed IFNγ-treated MSCs could generate ovalbumin-specific cytotoxic T lymphocytes (CTL). For this, splenocytes were isolated: from three immunized mice per group and restimulated in vitro with mitomycin C-treated ovalbumin-expressing E.G7 cells. Five days later, CD8+ T cells were purified from the reactivated splenocytes (>90% purity) and used as effectors in annexin-V-based CTL assays. Mice immunized with ovalbumin-pulsed IFNγ-treated MSCs developed a significant CD8-mediated ovalbumin-specific cytotoxic response (FIG. 7B). This experiment was repeated once with similar results. In order to test whether immunization induced systemic protective immunity, immunized mice were challenged with a subcutaneous injection of a tumorigeneic dose ($2 \times 10^6$ cells) of ovalbumin-expressing E.G7 tumor cells. Strikingly, 10 out of 10 mice immunized with ovalbumin-pulsed IFNγ-treated MSCs were fully protected against E.G7 tumors (FIG. 7C). In contrast, 1 out of 10 mice immunized with ovalbumin-pulsed IFNγ-treated MEF cells were protected (P<0.001 by Log Rank). Taken together, our data indicated that mouse MSCs are capable of efficient in vitro antigen presentation and can induce protective in vivo antigen-specific cellular immune responses.

Activation of MHC Class II-Restricted Hybridomas by IFNγ-Treated Human MSCs

Figure 8:
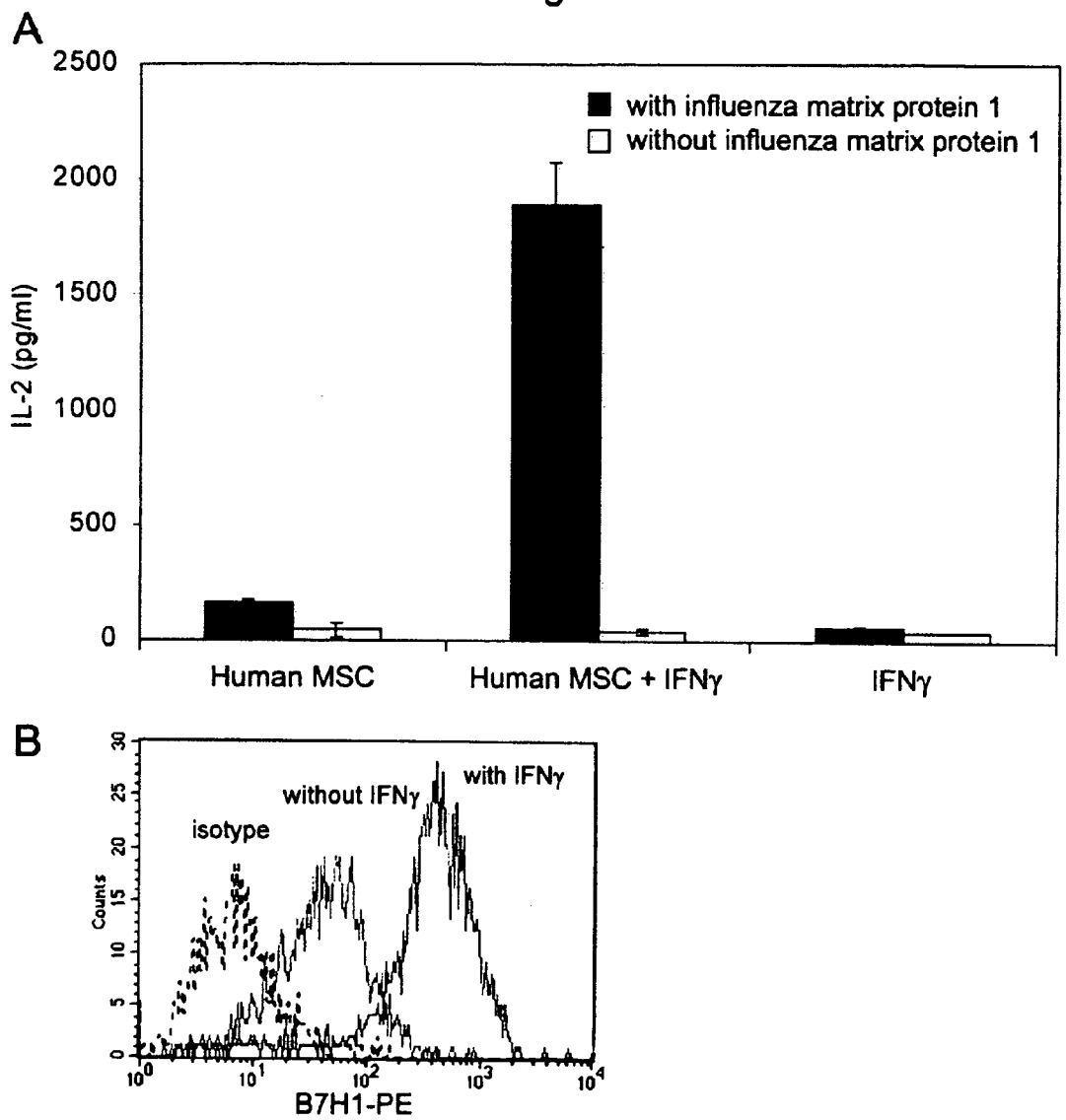
FIG. 8 shows Human MSCs-mediated activation of influenza M1-specific T-T hybridomas. (A) Bone marrow-derived DR1 positive human MSCs were treated or not for 24 hrs with recombinant human IFNγ (100 ng/ml) and subsequently cocultured for 24 hrs with influenza matrix protein-1-specific DR1-restricted T cell hybridomas in the presence or not of 100 μg/ml purified influenza matrix protein-1. Supernatant was collected and tested for IL-2 release by ELISA (Means of duplicates±standard deviations). (B) Human MSCs were analyzed by flow cytometry for B7-H1 surface expression before and after recombinant IFNγ treatment (100 ng/ml for 24 hrs). Plots show isotype control IgG staining profile (doted line) versus specific Ab staining profile (thick lines).

We assessed the ability of human MSCs to acquire antigen-presenting functions following IFNγ stimulation. Human MSCs were isolated from a healthy donor, culture expanded, HLA-typed and characterized by flow cytometry. When IFNγ-treated human MSCs were cocultured for 24 hrs with influenza matrix protein 1-specific DR1-restricted T-cell hybridomas in the presence of purified influenza matrix protein 1, significant levels of IL-2 was detected in the supernatant (FIG. 8A). IL-2 was not be detected when IFNγ-treated human MSCs were cocultured with hybridomas without the antigen, or when the hybridomas were cultured with the antigen and without human MSCs. This indicated that human MSCs can efficiently process exogenous antigens and present antigen-derived peptides to MHC class II restricted T cells. Furthermore, human MSCs significantly upregulated surface expression of the costimulatory molecule B7-H1 upon IFNγ stimulation (FIG. 8B). Taken together, our data suggested that human MSCs, similar to mouse MSCs, may behave as conditional antigen-presenting cells in syngeneic immune responses.

Animals and Cell Lines

Mice were 4-8 weeks old female C57BL/6 or BALB/c purchased from Charles River (LaPrairie, Qc, Canada). C57BL/6 mouse embryonic fibroblasts (MEF, SCRC-1008), EL4 and EL4-derived ovalbumin-expressing E.G7 cells were purchased from the American Type Culture Collection (Manassas, Va.). DC2.4 cells (C57BL/6 immortalized denditic cells), MF2.2D9 cells (MHC class II-restricted ovalbumin-specific T-T hybridomas) and RF33.70 cells (MHC class I-restricted ovalbumin-specific T-T hybridomas) have been described previously (Shen et al. J. Immunol. 1997 Mar. 15; 158(6):2723-30, incorporated herein by reference) and were a generous gift from Dr. Ken L. Rock (University of Massachusetts, Worcester). C57BL/6 ovalbumin-transgenic OT-II mice were kindly provided by Dr. C. Piccirillo (McGill University, Montreal, Canada). The anti-SIINFEKL/H2-K$^b$ mAb-producing hybridoma 25D1.16 (Porgador et al. Immunity. 1997 June; 6(6):715-26) was a gift from Dr. Ronald N. Germain (National Institute of Allergy and Infectious Diseases, Bethesda, Md.) and the mAb purified using Hi-Trap chromatography column (Amersham Biosciences). Synthetic SIINFEKL peptide was purchased from Sheldon Biotechnology Centre (McGill University). Purified influenza matrix protein 1 as well as humanized DR1-restricted influenza-specific T-T hybridomas have been described previously (Canaday et al. J Immunol Methods. 2003 Oct. 1; 281(1-2):129-42, incorporated herein by reference) and were a generous gift from Dr. David Canaday (Case Western Reserve University, Ohio).

Harvest of MSCs

Primary mouse MSCs were isolated from female C57BL/6 mice as previously described (Stagg et al. Hum Gene Ther. 2004 June; 15(6):597-608, incorporated herein by reference). Briefly, whole marrow from the femurs and tibias was flushed in DMEM (Wisent technologies, St-Bruno, QC, Canada) 10% fetal bovine serum (FBS) (Wisent technologies) and 50 U/ml Pen/Strep (Wisent technologies), plated for 5 days, washed and fresh media added to the adherent cells every 3-4 days. When 80% confluent, adherent cells were trypsinized (0.05% Trypsin, Wisent technologies, at 37° C. for 5 min), harvested and expanded until a homogenous population was obtain, i.e approximatively 20 population doublings, before being used for antigen presentation assays. Human MSCs were isolated as previously described (Jiang et al. Blood. 2005 May 15; 105(10):4120-6). Briefly, whole marrow was collected from patients undergoing hip surgery (Dr. J. Antoniou, Jewish General Hospital, Montreal, Canada), diluted in DMEM (Wisent technologies), centrifugated to remove the fatty layer, added to a Ficoll gradient (Amersham Bioscience, Oakville, ON, Canada) and centrifuged at 900 g for 30 minutes. Mononuclear cells were then washed in DMEM, counted and plated at $2 \times 10^5$ cells/cm$^2$ on 10 cm$^2$ tissue culture dishes in DMEM 10% FBS 50 U/ml Pen/Strep (Wisent technologies). The non-adherent cells were removed after 48 hours and media replaced every 3-4 days. When 80% confluent, adherent cells were trypsinized (0.05% Trypsin, Wisent technologies, at 37° C. for 5 min), harvested and expanded for a minimum of 10 population doublings before being used for flow cytometry analysis and antigen presentation assays. Human MSCs did not express CD45 or CD31, and were positive for CD105 and CD73 surface expression.

Differentiation of Mouse MSCs

MSCs were exposed to specific media to induce their differentiation. For osteogenic differentiation, MSCs were cultured in complete media supplemented with β-glycerol phosphate (10 mM), dexamethasone ($10^{-8}$ M) and ascorbic acid 2-phosphate (5 μg/ml) (all from Sigma-Aldrich, Oakville, ON, Canada) for 4 weeks renewing the media every 2-3 days. Alizarin Red S (2% pH 4.1 in ammonium hydroxide) was then used to stain calcium in the mineralized extracellular matrix. To induce adipogenic differentiation, MSCs were cultured in complete media supplemented with indomethacin (46 µM), 3-isobutyl-methylxanthine (0.5 mM), dexamethasone (1 µM) and insulin (10 µg/ml) (all from Sigma-Aldrich) for 7 days renewing the media twice and stained with oil-Red solution. Photographs of cells were taken under light microscopy using an Axiovert25 Zeiss microscope attached to a Contax167MT camera.

Flow Cytometry Analysis

Flow cytometry analysis was performed in PBS 2% FBS (Wisent Technologies) with the following mAbs: R-phycoerythrin (PE)-conjugated anti-mouse CD45 (clone 30-F11), H-2Kb (clone AF6-88.5), I-Ab (clone AF6-120.1), CD40 (clone 3/23), CD54 (clone 3E2), CD28 (clone 37.51; eBioscience, San Diego, Calif.), B7-DC (clone TY25; eBioscience), B7-H1 (clone MIH5; eBioscience) and 4-1BBL (clone TKS-1; eBioscience). Biotin-conjugated anti-mouse CD105 (clone MJ7/18; eBioscience), CD80 (clone 16-10A1), CD86 (clone PO3), ICOS-L (clone HK5.3). Isotypic control analyses were performed in parallel. Except where indicated, Abs are from BD Pharmingen (San Diego, Calif., USA). Biotinylated Abs were revealed by APC-streptavidin (BD Pharmingen). Flow cytometry was performed using a FACS Calibur cytometer (BD) and analyzed using Cellquest software.

Two-Way Mixed Lymphocytes Cultures

Splenocytes were isolated from C57BL/6 and BALB/c mice by mechanical dissociation of the spleens followed by red blood cells lysis (ammonium chloride 8.3 g/ml; Sigma-Aldrich). In triplicates, $10^5$ C57BL/6 splenocytes and $10^5$ BALB/c splenocytes per well were cocultured in a round-bottom 96-well plate in 200 µl complete medium (RPMI 10% FBS, 50 U/ml Pen-Strep; Wisent Technologies) with or without $10^5$ C57BL/6 MSCs, pretreated or not with recombinant mouse IFNγ (50 ng/ml; BioSource International, Camarillo, Calif.) for 20 hrs followed by extensive washing in PBS. After 3 days, the cocultures were centrifugated and 100 µl of supernatant was collected for measurement of mouse IFNγ using a commercial ELISA kit (R&D Systems, Minneapolis, Mo.).

Ovalbumin-Specific T-T Hybridoma Assays

DC2.4 or control MEF ($5\times10^4$ cells) were cocultured for 20 hrs with $10^5$ MF2.2D9 cells in flat-bottom 96-well plates in the presence or not of soluble ovalbumin (Sigma-Aldrich) at the indicated concentration in 200 µl complete media (RPMI 10% FBS 50 U/ml Pen/Strep; Wisent Technologies). Where indicated, $5\times10^4$ naïve or IFNγ-treated MSCs (50 ng/ml for 20 hrs) were added to the cocultures or in replacement of DC2.4 cells. Where indicated, recombinant mouse IFNγ was added to the cocultures (final 50 ng/ml). Where indicated, conditioned supernatant from naïve or IFNγ-treated MSCs (50 ng/ml for 20 hrs) were added to DC2.4 and MF2.2D9 cocultures. Where indicated, naïve or IFNγ-pretreated MSCs were fixed in 1% paraformaldehyde, washed once with DMEM (Wisent technologies), once with 0.125M D-L lysine buffer for 30 min (Sigma-Aldrich), four times with DMEM (Wisent technologies) and added to DC2.4 and MF2.2D9 cocultures. In some experiments, DC2.4 cells were first pulsed with soluble ovalbumin for 20 hrs and then cocultured with the indicated cells for another 20 hrs. Where indicated, MSCs were treated with chloroquine (100 µM; Sigma-Aldrich) 30 min prior to and during antigen exposure. After 20 hrs, supernatant was collected from the cocultures and tested for the presence of IL-2 by commercial ELISA (eBioscience).

OT-II Antigen Presentation Assays

C57BL/6 MSCs or DC2.4 were first pre-treated with recombinant mouse IFNγ (50 ng/ml) and soluble ovalbumin (2.5 mg/ml) for 20 hrs. The next day, ovalbumin-specific CD4+ T cells were isolated from the spleens and lymph nodes of transgenic OT-II mice using SpinSep™ kit following manufacturer's instructions (Stem Cell Technologies, Vancouver, Canada). IFNγ-treated ovalbumin-pulsed DC2.4 or MSCs ($5\times10^4$ cells) were then cocultured for 48 hrs with purified CD4+ OT-II cells in flat-bottom 96-well plates in 200 µl complete media (RPMI 10% FBS 50 U/ml Pen/Strep; Wisent Technologies). Where indicated, purified anti-mouse CD80 (clone 16-10A1) or isotype control Abs (50 µg/ml; BD Pharmingen) were added to the MSCs or DC2.4 30 min prior to and during coculture with OT-II cells. We then investigated whether CD80 expression on mouse MSCs was required for OT-II activation. After 48 hrs, supernatant was collected from the cocultures and tested for the presence of IL-2 by commercial ELISA (eBioscience)

In Vivo Immunization of Mice

C57BL/6 MSCs or MEF cells were treated in vitro with recombinant IFNγ (50 ng/ml) and soluble ovalbumin (2.5 mg/ml) for 20 hrs, washed with PBS and injected ($0.1\times10^6$ cells) intraperitonealy into syngeneic C57BL/6 mice. Two weeks later, the same mice were injected a second time with the corresponding cells ($0.2\times10^6$) and one week after, serum samples and splenocytes of immunized mice were collected. For antibodies titering, serum samples were diluted: in PBS, incubated for 2 hrs at 37° C. onto ovalbumin-coated (10 µg/ml) 96-well plates and revealed using anti-mouse Ig-HRP antibody (1:1000 in PBS 10% FBS; BD Pharmingen) and TMB substrate (eBioscience). For cytotoxic T cell assays (CTL), $50\times10^6$ pooled splenocytes from immunized mice were restimulated in vitro with $10^6$ Mitomycin-C (Sigma-Aldrich) treated E.G7 cells in complete media (RPMI 10% FBS 50 U/ml Pen/Strep, 50 µM β-mercaptoethanol) for 5 days. Then, CD8+ T cells were purified using SpinSep™ kit (Stem Cell Technologies) and used as effectors in annexin-V-based CTL assays against $5\times10^4$ PKH26-labelled (Sigma-Aldrich) EL4 or E.G7 targets and analyzed by flow cytometry as previously described (Stagg et al. Hum Gene Ther. 2004 June; 15(6):597-608 Fisher et al. J Immuno Methods. 2002; 259:159-169, incorporated herein by reference).

Human MSC Antigen Presentation Assay

Human MSCs preparations were HLA-typed (Montreal Royal Victoria tissue typing laboratory) and DR1 positive MSCs used in antigen presentation assays. Where indicated, human MSCs were pre-treated for 24 hrs with recombinant human IFNγ (100 ng/ml; InterMune Pharmaceuticals, Brisbane, Calif.) and subsequently cocultured for 24 hrs with influenza matrix protein-1-specific DR1-restricted T cell hybridomas and/or 100 µg/ml purified influenza matrix protein-1 in complete media (RPMI 10% FBS 50 U/ml Pen/Strep). After coculture, supernatant was collected and tested for mouse IL-2 release by ELISA (ebioscience).

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. An isolated interferonγ (IFNγ) stimulated stromal antigen-presenting cell wherein said isolated stromal antigen-presenting cell expresses MHC II and presents antigen in association with said MHC II, wherein said antigen is recognizable by T cells.

2. The stromal antigen-presenting cell as claimed in claim 1 which expresses B7-H1 molecules.

3. The stromal antigen-presenting cell as claimed in claim 1 which expresses CD80.

4. The stromal antigen presenting cell as claimed in claim 1 which is capable of inducing secretion of IL-2 by T cells.

5. The stromal antigen-presenting cell as claimed in claim 1 which is a bone marrow stromal antigen-presenting cell.

6. The stromal antigen-presenting cell as claimed in claim 5 which is a human stromal cell.

7. A stromal antigen-presenting cell produced by the method comprising:
 a) obtaining stromal cells from an animal;
 b) stimulating said cells with IFNγ; and
 c) contacting said stimulated cells with an antigen.

8. A composition comprising the stromal antigen-presenting cell as claimed in claim 1.

9. The composition as claimed in claim 8 further comprising a pharmaceutically acceptable carrier.

* * * * *